US006692962B1

(12) United States Patent
Roth

(10) Patent No.: US 6,692,962 B1
(45) Date of Patent: Feb. 17, 2004

(54) PLANT TRANSLATION METHODS AND COMPOSITIONS RELATED THERETO

(75) Inventor: Don A. Roth, Laramie, WY (US)

(73) Assignee: University of Wyoming, Laramie, WY (US)

( * ) Notice: Subject to any disclaimer, the term of this patent is extended or adjusted under 35 U.S.C. 154(b) by 52 days.

(21) Appl. No.: 09/587,789

(22) Filed: Jun. 6, 2000

(51) Int. Cl.$^{7}$ ............................ C12N 5/04; C12N 5/00; C12N 15/82; C07H 21/04; A61K 38/16

(52) U.S. Cl. ........................... 435/419; 435/6; 435/410; 435/468; 530/352; 530/375; 536/23.1; 536/23.6

(58) Field of Search .......................... 435/6, 69.2, 91.1, 435/468, 375; 536/23.1, 23.6, 24.1, 24.5

(56) References Cited

PUBLICATIONS

Jeffrey O. Langland et al., Phosphorylation of Plant Eukaryotic Intiation Factor–2 by the Plant–encoded Double–stranded RNA–dependent Protein Synthesis in Vitro, Journal of Biological Chemistry, vol. 271, No. 8, pp. 4539–4544.*

Daniel R. Gallie et al., Translation initiation factors are differentially regulated in cereals during development and following heat shock, The Plant Journal (1998), 14, (16), pp. 715–722.*

Shimian Qu et al., Isolation and characterization of the Drosophila melanogaster eIF—2x gene encoding the alpha subunit of translation initiation factor eIF–2, Gene, 140 (1994), pp. 239–242.*

Horsch, et al., A5 *Plant Molecular Biology Manual* 1–9 (1988).

Kaufman, et al., 9–3 *Mol. Cell Biol.* 946–958 (1989).

Murtha–Reil, et al., vol. 268, No. 17, Issue of Jun. 15, *The Journal of Biological Chemistry* 12946–12951 (1993).

Chang, et al., 41 *Plant Molecular Biology* 363–370 (1999).

* cited by examiner

*Primary Examiner*—Sean McGarry
*Assistant Examiner*—Jane Zara
(74) *Attorney, Agent, or Firm*—Dann, Dorfman, Herrell and Skillman

(57) ABSTRACT

The present invention relates to the field of plant molecular biology, in particular to translational control. The inventors herein disclose compositions and methods useful to alter plant gene translation, which methods enable genetic modification of numerous plant processes, such as inducible or constitutive responses to biotic and abiotic stress, or growth pattern adjustment.

16 Claims, 4 Drawing Sheets

(2 of 4 Drawing Sheet(s) Filed in Color)

SEQUENCE LISTING

```
<160> NUMBER OF SEQ ID NOS:  15

<210> SEQ ID NO 1
<211> LENGTH: 340
<212> TYPE: PRT
<213> ORGANISM: Triticum aestivum

<400> SEQUENCE: 1

Met Ala Asn Leu Glu Cys Arg Met Tyr Glu Pro Arg Phe Pro Glu Val
  1               5                  10                  15

Asp Ala Ala Val Met Ile Gln Val Lys His Ile Ala Asp Met Gly Ala
             20                  25                  30

Tyr Val Ser Leu Leu Glu Tyr Asn Asn Val Glu Gly Met Ile Leu Phe
         35                  40                  45

Ser Glu Leu Ser Arg Arg Arg Ile Arg Ser Ile Ser Ser Leu Ile Lys
     50                  55                  60

Val Gly Arg Gln Glu Pro Ala Ile Val Leu Arg Val Asp Arg Asp Lys
 65                  70                  75                  80

Gly Tyr Ile Asp Leu Ser Lys Arg Arg Val Ser Glu Glu Glu Ala Arg
                 85                  90                  95

Ser Cys Glu Asp Lys Tyr Asn Lys Ser Lys Leu Val His Ser Ile Met
            100                 105                 110

Arg His Val Ala Glu Thr Leu Glu Ile Asp Leu Glu Pro Ile Tyr Gln
        115                 120                 125

Arg Ile Gly Trp Pro Leu Tyr Arg Lys Tyr Gly His Ala Phe Glu Ala
    130                 135                 140
```

-continued

```
Phe Lys Leu Ile Val Ala Asp Pro Asp Ala Ile Leu Asp Val Leu Thr
145                 150                 155                 160

Tyr Glu Glu Arg Glu Thr Gly Pro Asp Gly Gln Glu Val Thr Lys Val
                165                 170                 175

Val Pro Ala Val Thr Pro Glu Ile Lys Glu Thr Leu Val Gln Asn Ile
            180                 185                 190

Arg Arg Arg Met Thr Pro Gln Pro Leu Lys Ile Arg Ala Asp Val Glu
        195                 200                 205

Met Lys Cys Phe Gln Phe Asp Gly Val Leu His Ile Lys Gln Ala Met
    210                 215                 220

Arg Lys Ala Glu Ala Ala Gly Asn Thr Asn Cys Pro Val Lys Ile Lys
225                 230                 235                 240

Leu Val Ala Pro Pro Pro Leu Tyr Val Leu Thr Thr Gln Thr Leu Asp
                245                 250                 255

Lys Asp Gln Gly Ile Ser Val Leu Thr Asp Ala Val Lys Ala Cys Thr
            260                 265                 270

Ala Glu Ile Glu Lys His Lys Gly Lys Leu Val Val Lys Glu Ala Pro
        275                 280                 285

Arg Ala Val Ser Glu Arg Glu Asp Lys Leu Leu Asn Ala Gln Leu Asp
    290                 295                 300

Thr Leu Val Glu Gln Asn Ala Glu Val Ala Gly Asp Asp Asp Ser Glu
305                 310                 315                 320

Asp Glu Glu Asp Thr Gly Met Gly Asp Ile Asp Leu Thr Asn Ser Gly
                325                 330                 335

Val His Ala Asp
            340
```

<210> SEQ ID NO 2
<211> LENGTH: 1188
<212> TYPE: DNA
<213> ORGANISM: Triticum aestivum

<400> SEQUENCE: 2

```
cttcttcttg cgcccgctcg gcagaaattg tacacgtttt tcatttcgaa aagtccaaat     60

tgcccatttt ttggccatag accacagact ttaacatggc cctgacgtcg cgcttctaca    120

acgagcggta tccggagatc gaggatgtcg ttatggtgaa cgtgctgtcc atcgccgaga    180

tgggcgccta cgttcatctg cttgagtaca acaacatcga gggcatgatc ctgctgtcgg    240

agctgtcccg ccggcgcatc cgctccatca acaagctgat tcgtgtcggc aagaccgaac    300

cggtggtggt tatccgtgtt gacaaggaga agggctacat cgatctgtcg aagcgtcgcg    360

tttcgcccga agatgtcgag aagtgcaccg agcgcttcgc taaggccaag gccatcaact    420

cactgctccg ccatgtcgcc gacatactcg gcttcgaggg caacgagaag ctggaagatc    480

tctaccagaa gaccgcctgg cacttcgaga agaagtacaa caacaagacg gtcgcctacg    540

acatcttcaa gcaatcggtc accgatccca ccgtcttcga tgagtgcaac ctggaaccgg    600

agaccaagga ggtcctgttg agcaacatca agcggaagct ggtctcgccc actgtcaaga    660

tccgtgcgga catcgagtgc tcctgctacg gttacgaggg catcgacgct gtcaaggcat    720

cgctcaccaa gggcctggag ctgagcaccg aggagctgcc cattcgcatc aacctgatag    780

caccgccact ctatgtaatg accacatcca ctaccaagaa gacagacggt ttaaaggctc    840

tggaggtggc cattgagcac attcgcgcca agaccagcga gtacgatgga gagttcaagg    900

tgatcatggc acccaaactg gttacggcca tcgacgaggc ggatctggcc agacgcctgg    960
```

-continued

```
agcgcgctga ggccgagaac gcccaggtgg ctggcgacga tgacgaggag gatggcgccg   1020

accaggaggg catgcagttc gatccagaga aggagttcaa ccacaaggga tcgggggcgg   1080

gtcgtgcgaa cgaggaggat gaggaggagg aagaggatta gcgtagccac agcatcagac   1140

acaactatag caactgtaac aaacaattaa aggagttttg caaaaatc                1188
```

<210> SEQ ID NO 3
<211> LENGTH: 315
<212> TYPE: PRT
<213> ORGANISM: Homo sapiens

<400> SEQUENCE: 3

```
Met Pro Gly Leu Ser Cys Arg Phe Tyr Gln His Lys Phe Pro Glu Val
  1               5                  10                  15

Glu Asp Val Val Met Val Asn Val Arg Ser Ile Ala Glu Met Gly Ala
             20                  25                  30

Tyr Val Ser Leu Leu Glu Tyr Asn Asn Ile Glu Gly Met Ile Leu Leu
         35                  40                  45

Ser Glu Leu Ser Arg Arg Arg Ile Arg Ser Ile Asn Lys Leu Ile Arg
     50                  55                  60

Ile Gly Arg Asn Glu Cys Val Val Val Ile Arg Val Asp Lys Glu Lys
 65                  70                  75                  80

Gly Tyr Ile Asp Leu Ser Lys Arg Arg Val Ser Pro Glu Glu Ala Ile
                 85                  90                  95

Lys Cys Glu Asp Lys Phe Thr Lys Ser Lys Thr Val Tyr Ser Ile Leu
            100                 105                 110

Arg His Val Ala Glu Val Leu Glu Tyr Thr Lys Asp Glu Gln Leu Glu
        115                 120                 125

Ser Leu Phe Gln Arg Thr Ala Trp Val Phe Asp Asp Lys Tyr Lys Arg
    130                 135                 140

Pro Gly Tyr Gly Ala Tyr Asp Ala Phe Lys His Ala Val Ser Asp Pro
145                 150                 155                 160

Ser Ile Leu Asp Ser Leu Asp Leu Asn Glu Asp Glu Arg Glu Val Leu
                165                 170                 175

Ile Asn Asn Ile Asn Arg Arg Leu Thr Pro Gln Ala Val Lys Ile Arg
            180                 185                 190

Ala Asp Ile Glu Val Ala Cys Tyr Gly Tyr Glu Gly Ile Asp Ala Val
        195                 200                 205

Lys Glu Ala Leu Arg Ala Gly Leu Asn Cys Ser Thr Glu Asn Met Pro
    210                 215                 220

Ile Lys Ile Asn Leu Ile Ala Pro Pro Arg Tyr Val Met Thr Thr Thr
225                 230                 235                 240

Thr Leu Glu Arg Thr Glu Gly Leu Ser Val Leu Ser Gln Ala Met Ala
                245                 250                 255

Val Ile Lys Glu Lys Ile Glu Glu Lys Arg Gly Val Phe Asn Val Gln
            260                 265                 270

Met Glu Pro Lys Val Val Thr Asp Thr Asp Glu Thr Glu Leu Ala Arg
        275                 280                 285

Gln Met Glu Arg Leu Glu Arg Glu Asn Ala Glu Val Asp Gly Asp Asp
    290                 295                 300

Asp Ala Glu Glu Met Glu Ala Lys Ala Glu Asp
305                 310                 315
```

<210> SEQ ID NO 4
<211> LENGTH: 1393

-continued

<212> TYPE: DNA
<213> ORGANISM: Homo sapiens

<400> SEQUENCE: 4

```
gtgcgggaat cacacacata cctcagaatg ccgggtctaa gttgtagatt ttatcaacac     60
aaatttcctg aggtggaaga tgtagtgatg gtgaatgtca gatccattgc tgaaatgggg    120
gcttatgtca gcttgctgga atacaacaac attgaaggca tgattcttct tagtgaatta    180
tccagaaggc gtatccgttc tatcaacaaa ctcatccgaa ttggcaggaa tgagtgtgtg    240
gttgtcatta gggtggacaa agaaaaagga tatattgatt tgtcaaaaag aagagtttct    300
ccagaggaag caatcaaatg tgaagacaaa ttcacaaaat ccaaaactgt ttatagcatt    360
cttcgtcatg ttgctgaggt gttagaatac accaaggatg agcagctgga aagcctattc    420
cagaggactg cctgggtctt tgatgacaag tacaagagac ctggatatgg tgcctatgat    480
gcatttaagc atgcagtctc agacccatct attttggata gtttagattt gaatgaagat    540
gaacgggaag tactcattaa taatattaat aggcgcttga ccccacaggc tgtcaaaatt    600
cgagcagata ttgaagtggc ttgttatggt tatgaaggca ttgatgctgt aaaagaagcc    660
ctaagagcag gtttgaattg ttctacagaa aacatgccca ttaagattaa tctaatagct    720
cctcctcggt atgtaatgac tacgacaacc ctggagagaa cagaaggcct ttctgtcctc    780
agtcaagcta tggctgttat caaagagaag attgaggaaa agaggggtgt gttcaatgtt    840
caaatggagc ccaaagtggt cacagataca gatgagactg aacttgcgag gcagatggag    900
aggcttgaaa gagaaaatgc cgaagtggat ggagatgatg atgcagaaga aatggaagcc    960
aaagctgaag attaactttg tgggaaacag agtccaattt aaggaacaca gagcagcgct   1020
tcctggctgt aaatcctaga cttgaaagtt ttccagtatt gaaaacttca aagctgaata   1080
ttttttattt ctaagtattt aaatgttcta acagatcaga acatgaaatg ccctcctaaa   1140
tgtcagctgt tgtcacacag tagctccaac actttgagca tttttaaggg agtggcctca   1200
tttcactaga gacaaatctt taagaatagt tctaaaattg ggcttgtgat ttccatttct   1260
gatgtctcca gattggcacc cctttctagt tcaatgcctc acgagatttg ccaggggcat   1320
ccaaggcaaa caatcccaat ctttctatat aaaatgtatt caagcaaaca tcaaataaat   1380
ttctgggata ttt                                                      1393
```

<210> SEQ ID NO 5
<211> LENGTH: 315
<212> TYPE: PRT
<213> ORGANISM: Homo sapiens

<400> SEQUENCE: 5

```
Met Pro Gly Leu Ser Cys Arg Phe Tyr Gln His Lys Phe Pro Glu Val
  1               5                  10                  15

Glu Asp Val Val Met Val Asn Val Arg Ser Ile Ala Glu Met Gly Ala
             20                  25                  30

Tyr Val Ser Leu Leu Glu Tyr Asn Asn Ile Glu Gly Met Ile Leu Leu
         35                  40                  45

Ser Glu Leu Ser Arg Arg Arg Ile Arg Ser Ile Asn Lys Leu Ile Arg
     50                  55                  60

Ile Gly Arg Asn Glu Cys Val Val Val Ile Arg Val Asp Lys Glu Lys
 65                  70                  75                  80

Gly Tyr Ile Asp Leu Ser Lys Arg Arg Val Ser Pro Glu Glu Ala Ile
                 85                  90                  95
```

-continued

```
Lys Cys Glu Asp Lys Phe Thr Lys Ser Lys Thr Val Tyr Ser Ile Leu
            100                 105                 110

Arg His Val Ala Glu Val Leu Glu Tyr Thr Lys Asp Glu Gln Leu Glu
        115                 120                 125

Ser Leu Phe Gln Arg Thr Ala Trp Val Phe Asp Asp Lys Tyr Lys Arg
    130                 135                 140

Pro Gly Tyr Gly Ala Tyr Asp Ala Phe Lys His Ala Val Ser Asp Pro
145                 150                 155                 160

Ser Ile Leu Asp Ser Leu Asp Leu Asn Glu Asp Glu Arg Glu Val Leu
                165                 170                 175

Ile Asn Asn Ile Asn Arg Arg Leu Thr Pro Gln Ala Val Lys Ile Arg
            180                 185                 190

Ala Asp Ile Glu Val Ala Cys Tyr Gly Tyr Glu Gly Ile Asp Ala Val
        195                 200                 205

Lys Glu Ala Leu Arg Ala Gly Leu Asn Cys Ser Thr Glu Asn Met Pro
    210                 215                 220

Ile Lys Ile Asn Leu Ile Ala Pro Pro Arg Tyr Val Met Thr Thr Thr
225                 230                 235                 240

Thr Leu Glu Arg Thr Glu Gly Leu Ser Val Leu Ser Gln Ala Met Ala
                245                 250                 255

Val Ile Lys Glu Lys Ile Glu Glu Lys Arg Gly Val Phe Asn Val Gln
            260                 265                 270

Met Glu Pro Lys Val Val Thr Asp Thr Asp Glu Thr Glu Leu Ala Arg
        275                 280                 285

Gln Met Glu Arg Leu Glu Arg Glu Asn Ala Glu Val Asp Gly Asp Asp
    290                 295                 300

Asp Ala Glu Glu Met Glu Ala Lys Ala Glu Asp
305                 310                 315
```

<210> SEQ ID NO 6
<211> LENGTH: 1393
<212> TYPE: DNA
<213> ORGANISM: Homo sapiens

<400> SEQUENCE: 6

```
gtgcgggaat cacacacata cctcagaatg ccgggtctaa gttgtagatt ttatcaacac     60

aaatttcctg aggtggaaga tgtagtgatg gtgaatgtca gatccattgc tgaaatgggg    120

gcttatgtca gcttgctgga atacaacaac attgaaggca tgattcttct tagtgaatta    180

tccagaaggc gtatccgttc tatcaacaaa ctcatccgaa ttggcaggaa tgagtgtgtg    240

gttgtcatta gggtggacaa agaaaaagga tatattgatt tgtcaaaaag aagagtttct    300

ccagaggaag caatcaaatg tgaagacaaa ttcacaaaat ccaaaactgt ttatagcatt    360

cttcgtcatg ttgctgaggt gttagaatac accaaggatg agcagctgga aagcctattc    420

cagaggactg cctgggtctt tgatgacaag tacaagagac ctggatatgg tgcctatgat    480

gcatttaagc atgcagtctc agacccatct attttggata gtttagattt gaatgaagat    540

gaacgggaag tactcattaa taatattaat aggcgcttga ccccacaggc tgtcaaaatt    600

cgagcagata ttgaagtggc ttgttatggt tatgaaggca ttgatgctgt aaaagaagcc    660

ctaagagcag gtttgaattg ttctacagaa aacatgccca ttaagattaa tctaatagct    720

cctcctcggt atgtaatgac tacgacaacc ctggagagaa cagaaggcct ttctgtcctc    780

agtcaagcta tggctgttat caaagagaag attgaggaaa agagggtgt gttcaatgtt     840

caaatggagc ccaaagtggt cacagataca gatgagactg aacttgcgag gcagatggag    900
```

-continued

```
aggcttgaaa gagaaaatgc cgaagtggat ggagatgatg atgcagaaga aatggaagcc    960

aaagctgaag attaactttg tgggaaacag agtccaattt aaggaacaca gagcagcgct   1020

tcctggctgt aaatcctaga cttgaaagtt ttccagtatt gaaaacttca aagctgaata   1080

ttttttattt ctaagtattt aaatgttcta acagatcaga acatgaaatg ccctcctaaa   1140

tgtcagctgt tgtcacacag tagctccaac actttgagca tttttaaggg agtggcctca   1200

tttcactaga gacaaatctt taagaatagt tctaaaattg ggcttgtgat ttccatttct   1260

gatgtctcca gattggcacc cctttctagt tcaatgcctc acgagatttg ccaggggcat   1320

ccaaggcaaa caatcccaat ctttctatat aaaatgtatt caagcaaaca tcaaataaat   1380

ttctgggata ttt                                                      1393


<210> SEQ ID NO 7
<211> LENGTH: 315
<212> TYPE: PRT
<213> ORGANISM: Danio rerio

<400> SEQUENCE: 7

Met Pro Gly Leu Ser Cys Arg Phe Tyr Gln His Arg Phe Pro Glu Val
  1               5                  10                  15

Glu Asp Val Val Met Val Asn Val Arg Ser Ile Ala Glu Met Gly Ala
             20                  25                  30

Tyr Val Ser Leu Leu Glu Tyr Asn Asn Ile Glu Gly Met Ile Leu Leu
         35                  40                  45

Ser Glu Leu Ser Arg Arg Arg Ile Arg Ser Ile Asn Lys Leu Ile Arg
     50                  55                  60

Ile Gly Arg Asn Glu Cys Val Val Val Ile Arg Val Asp Lys Glu Lys
 65                  70                  75                  80

Gly Tyr Ile Asp Leu Ser Lys Arg Arg Val Ser Pro Glu Glu Ala Ile
                 85                  90                  95

Lys Cys Glu Asp Lys Phe Thr Lys Ser Lys Thr Val Tyr Ser Ile Leu
            100                 105                 110

Arg His Val Ala Glu Val Leu Glu Tyr Thr Lys Asp Glu Gln Leu Glu
        115                 120                 125

Ser Leu Phe Gln Arg Thr Ala Trp Val Phe Asp Glu Lys Tyr Lys Lys
    130                 135                 140

Pro Gly Tyr Gly Ala Tyr Asp Val Phe Lys Gln Ala Val Ser Asp Pro
145                 150                 155                 160

Ala Ile Leu Asp Gly Leu Asp Leu Thr Glu Glu Glu Arg Asn Val Leu
                165                 170                 175

Ile Asp Asn Ile Asn Arg Arg Leu Thr Pro Gln Ala Val Lys Ile Arg
            180                 185                 190

Ala Asp Ile Glu Val Ala Cys Tyr Gly Tyr Glu Gly Ile Asp Ala Val
        195                 200                 205

Lys Glu Ala Leu Arg Ala Gly Leu Asn Cys Ser Thr Glu Ala Met Pro
    210                 215                 220

Ile Lys Ile Asn Leu Ile Ala Pro Pro Arg Tyr Val Met Thr Thr Thr
225                 230                 235                 240

Thr Leu Glu Arg Thr Glu Gly Leu Ser Val Leu Asn Gln Ala Met Ala
                245                 250                 255

Ala Ile Lys Glu Arg Ile Glu Glu Lys Arg Gly Val Phe Asn Val Gln
            260                 265                 270

Met Glu Pro Lys Val Val Thr Asp Thr Asp Glu Thr Glu Leu Gln Arg
```

-continued

```
        275                 280                 285

Gln Leu Glu Arg Leu Glu Arg Glu Asn Ala Glu Val Asp Gly Asp Asp
    290                 295                 300

Asp Ala Glu Glu Met Glu Ala Lys Thr Glu Asp
305                 310                 315


<210> SEQ ID NO 8
<211> LENGTH: 948
<212> TYPE: DNA
<213> ORGANISM: Danio rerio

<400> SEQUENCE: 8

atgccgggtc taagctgtag attttaccag caccgcttcc ccgaggtgga ggacgtggtg      60

atggtgaacg tgcgctcgat cgctgagatg ggagcgtatg tgagtctgct ggagtacaac     120

aacatcgagg gcatgatcct gctgagcgaa ctgtcccgca gacgcatccg ctccatcaac     180

aaactcatcc gcatcggacg caacgagtgt gtggtggtca tcagggtgga caaggagaag     240

ggttacattg atctgtccaa gagaagagtg tctccagaag aagccatcaa atgcgaggat     300

aaattcacca aatctaaaac cgtgtacagt attttgcggc acgtggctga ggtgttggag     360

tacaccaaag acgagcagct ggagagtttg ttccagagaa ccgcttgggt ttttgatgag     420

aaatacaaga agcctggata cggggcctac gacgtcttta aacaagctgt gtctgatcct     480

gccattctgg atggtttgga tctgactgag gaagagagaa acgtgctcat cgacaacatc     540

aacaggcgac tcacaccaca ggccgtcaaa ataagagctg acattgaggt ggcgtgttat     600

ggatatgaag gcatcgatgc agtgaaggag gctctgaggg caggactcaa ttgctccact     660

gaagccatgc ctatcaagat caacctgatc gcgccgccgc ggtacgtcat gaccaccaca     720

acactggagc gaacagaagg cctgtcagtg ctcaaccagg ccatggccgc aattaaagag     780

cggatcgagg agaagcgagg agtcttcaat gtgcagatgg agcccaaggt ggtgacggac     840

acagacgaga cggaactgca gcggcagctc gagcgtctgg agcgagaaaa cgcagaagtg     900

gacggagacg acgatgcaga agagatggag gccaaaactg aggactag                  948


<210> SEQ ID NO 9
<211> LENGTH: 315
<212> TYPE: PRT
<213> ORGANISM: Rattus sp.

<400> SEQUENCE: 9

Met Pro Gly Leu Ser Cys Arg Phe Tyr Gln His Lys Phe Pro Glu Val
  1               5                  10                  15

Glu Asp Val Val Met Val Asn Val Arg Ser Ile Ala Glu Met Gly Ala
             20                  25                  30

Tyr Val Ser Leu Leu Glu Tyr Asn Asn Ile Glu Gly Met Ile Leu Leu
         35                  40                  45

Ser Glu Leu Ser Arg Arg Arg Ile Arg Ser Ile Asn Lys Leu Ile Arg
     50                  55                  60

Ile Gly Arg Asn Glu Cys Val Val Val Ile Arg Val Asp Lys Glu Lys
 65                  70                  75                  80

Gly Tyr Ile Asp Leu Ser Lys Arg Arg Val Ser Pro Glu Glu Ala Ile
                 85                  90                  95

Lys Cys Glu Asp Lys Phe Thr Lys Ser Lys Thr Val Tyr Ser Ile Leu
            100                 105                 110

Arg His Val Ala Glu Val Leu Glu Tyr Thr Lys Asp Glu Gln Leu Glu
        115                 120                 125
```

-continued

```
Ser Leu Phe Gln Arg Thr Ala Trp Val Phe Asp Asp Lys Tyr Lys Arg
    130                 135                 140

Pro Gly Tyr Gly Ala Tyr Asp Ala Phe Lys His Ala Val Ser Asp Pro
145                 150                 155                 160

Ser Ile Leu Asp Ser Leu Asp Leu Asn Glu Asp Glu Arg Glu Val Leu
                165                 170                 175

Ile Asn Asn Ile Asn Arg Arg Leu Thr Pro Gln Ala Val Lys Ile Arg
            180                 185                 190

Ala Asp Ile Glu Val Ala Cys Tyr Gly Tyr Glu Gly Ile Asp Ala Val
        195                 200                 205

Lys Glu Ala Leu Arg Ala Gly Leu Asn Cys Ser Thr Glu Thr Met Pro
    210                 215                 220

Ile Lys Ile Asn Leu Ile Ala Pro Pro Arg Tyr Val Met Thr Thr Thr
225                 230                 235                 240

Thr Leu Glu Arg Thr Glu Gly Leu Ser Val Leu Asn Gln Ala Met Ala
                245                 250                 255

Val Ile Lys Glu Lys Ile Glu Glu Lys Arg Gly Val Phe Asn Val Gln
            260                 265                 270

Met Glu Pro Lys Val Val Thr Asp Thr Asp Glu Thr Glu Leu Ala Arg
        275                 280                 285

Gln Leu Glu Arg Leu Glu Arg Glu Asn Ala Glu Val Asp Gly Asp Asp
    290                 295                 300

Asp Ala Glu Glu Met Glu Ala Lys Ala Glu Asp
305                 310                 315


<210> SEQ ID NO 10
<211> LENGTH: 1377
<212> TYPE: DNA
<213> ORGANISM: Rattus sp.

<400> SEQUENCE: 10

gttcgggatt cacacataca cttcagaatg ccgggtctaa gttgtagatt ttatcaacac      60

aaatttcctg aggtcgaaga tgtagtgatg gtgaatgtaa gatccattgc tgaaatgggg     120

gcctatgtca gcttgttgga atataataac attgaaggca tgattcttct tagtgaatta     180

tccagacgac gtatccgttc tataaacaaa ctgatccgaa ttggcagaaa tgaatgtgta     240

gttgtcatta gagtggataa agaaaaagga tatatagatt tgtcaaaaag aagagtttct     300

ccagaggaag caatcaaatg tgaagacaaa ttcacaaaat ccaaaactgt ttatagcatt     360

cttcgccatg ttgctgaggt attagagtat accaaggatg agcagctgga aagcctattc     420

cagaggactg cctgggtctt tgatgacaag tacaagagac ctggatatgg tgcctatgat     480

gcctttaagc atgcagtctc agacccatct atcttggata gtttagattt gaatgaagat     540

gaaagagaag tactcattaa caatatcaat aggcgtttga ccccacaagc tgtcaagatt     600

cgagcagata ttgaggtagc ttgctatggt tacgaaggca ttgatgctgt aaaagaagcc     660

ctgagagcag gtttgaattg ttctacagaa accatgccca tcaagattaa tctaatagct     720

ccacccaggt atgtgatgac aacaacgacc ctagagagga cagaaggact ctctgttctc     780

aatcaggcta tggcagtcat caaagaaaag attgaggaga agaggggagt gttcaatgtt     840

cagatggagc ccaaagtggt tacagataca gatgagactg aacttgcaag gcagctggaa     900

cggcttgaga gagaaaatgc agaagtggat ggagatgatg atgcagaaga aatggaagcc     960

aaagctgaag attaaccttt tggaaaacag tccaatttaa ggagtacgaa gcagcccttt    1020
```

-continued

```
ctggctgtaa accctagact tgaaagtttt ccagtattga aaacttcaaa gctgaatatt   1080

tttatttcca agtatttaag tattcgacaa gccagaatct aaatgccctc cttcatgtca   1140

gctgttttca catagtggct ctaacacctc aagcgttttt aagggagtgg cttgatttga   1200

ccagagacaa atgttaaacc gcagtcctaa aattgggctt gcggttttca tttctgatgt   1260

ctctggattg gcacccttat ggtttagaga attaccaggg gctccagaca ccaacaatcc   1320

caacctttct atataaaatg tactcaagca aacatcaaat aaatttctgg gatattt      1377
```

```
<210> SEQ ID NO 11
<211> LENGTH: 304
<212> TYPE: PRT
<213> ORGANISM: Saccharomyces sp.

<400> SEQUENCE: 11

Met Ser Thr Ser His Cys Arg Phe Tyr Glu Asn Lys Tyr Pro Glu Ile
  1               5                  10                  15

Asp Asp Ile Val Met Val Asn Val Gln Gln Ile Ala Glu Met Gly Ala
             20                  25                  30

Tyr Val Lys Leu Leu Glu Tyr Asp Asn Ile Glu Gly Met Ile Leu Leu
         35                  40                  45

Ser Glu Leu Ser Arg Arg Arg Ile Arg Ser Ile Gln Lys Leu Ile Arg
     50                  55                  60

Val Gly Lys Asn Asp Val Ala Val Val Leu Arg Val Asp Lys Glu Lys
 65                  70                  75                  80

Gly Tyr Ile Asp Leu Ser Lys Arg Arg Val Ser Ser Glu Asp Ile Ile
                 85                  90                  95

Lys Cys Glu Glu Lys Tyr Gln Lys Ser Lys Thr Val His Ser Ile Leu
            100                 105                 110

Arg Tyr Cys Ala Glu Lys Phe Gln Ile Pro Leu Glu Glu Leu Tyr Lys
        115                 120                 125

Thr Ile Ala Trp Pro Leu Ser Arg Lys Phe Gly His Ala Tyr Glu Ala
    130                 135                 140

Phe Lys Leu Ser Ile Ile Asp Glu Thr Val Trp Glu Gly Ile Glu Pro
145                 150                 155                 160

Pro Ser Lys Asp Val Leu Asp Glu Leu Lys Asn Tyr Ile Ser Lys Arg
                165                 170                 175

Leu Thr Pro Gln Ala Val Lys Ile Arg Ala Asp Val Glu Val Ser Cys
            180                 185                 190

Phe Ser Tyr Glu Gly Ile Asp Ala Ile Lys Asp Ala Leu Lys Ser Ala
        195                 200                 205

Glu Asp Met Ser Thr Glu Gln Met Gln Val Lys Val Lys Leu Val Ala
    210                 215                 220

Ala Pro Leu Tyr Val Leu Thr Thr Gln Ala Leu Asp Lys Gln Lys Gly
225                 230                 235                 240

Ile Glu Gln Leu Glu Ser Ala Ile Glu Lys Ile Thr Glu Val Ile Thr
                245                 250                 255

Lys Tyr Gly Gly Val Cys Asn Ile Thr Met Pro Pro Lys Ala Val Thr
            260                 265                 270

Ala Thr Glu Asp Ala Glu Leu Gln Ala Leu Leu Glu Ser Lys Glu Leu
        275                 280                 285

Asp Asn Arg Ser Asp Ser Glu Asp Asp Glu Asp Glu Ser Asp Asp Glu
    290                 295                 300

<210> SEQ ID NO 12
```

-continued

<211> LENGTH: 1764
<212> TYPE: DNA
<213> ORGANISM: Saccharomyces sp.

<400> SEQUENCE: 12

```
ataaaacaag gaataatttc cacatagata tgcaattaag ttttatatgt aaaagtgagc     60
attcatcgtt cagctcaaaa tacgtttctt gtcacagctg gtagaaaaac tatgagcgtt    120
ttttcttacc cgcagtcgga gaaaaatttt ttcttcgaag aggcgaaaaa gagaagaaga    180
gaaagcacaa atctgatgaa atagtagtat aaaatcgcat ttacaaattt tcaaccattg    240
tttatttcct aggtcattaa agagtaaagt gcaatctgtt tactaatcag tttttgtctt    300
catatttttg tgtcttttct gctgcctcac gcaccttcta taatacacca aataatgtcc    360
acttctcatt gcagatttta tgaaaacaaa tacccagaaa ttgacgatat cgtcatggtt    420
aacgtccagc agattgctga aatgggtgct tatgttaaat tgttagaata tgacaacatt    480
gaaggtatga ttctactaag tgaattgtcc cgtagacgta ttaggtcaat ccaaaaatta    540
attcgtgttg gtaaaaatga tgtcgccgtt gttcttcgtg tcgacaaaga aaaaggttat    600
attgatttgt ccaaacgtcg tgtttcttct gaagatatca ttaaatgtga agaaaaatac    660
caaaaatcta agactgttca ttccatttta agatactgtg ccgaaaaatt ccaaatccct    720
ttggaagaac tatataagac cattgcttgg ccattaagtc gaaaatttgg tcacgcttac    780
gaagctttca aactatccat cattgacgaa actgtttggg aaggtattga accgccatca    840
aaagatgttt tagatgaatt aaagaactat atctccaaga gattaacacc acaagctgta    900
aagattagag ccgatgttga agtgtcttgt tttagttacg aaggtatcga tgccattaaa    960
gacgcattaa aatcagctga agacatgtcc acagaacaaa tgcaagttaa agttaaatta   1020
gtcgccgccc cattatatgt tttgaccacc caagccttgg ataagcaaaa aggtattgaa   1080
caactggaaa gcgctattga aaaaattaca gaggttatta caaaatacgg cggtgtttgc   1140
aacattacca tgccaccaaa ggctgtcact gctactgaag acgctgagtt acaagctcta   1200
ttagaaagca aagaattaga taatagatct gactctgaag acgatgagga tgagtcagac   1260
gacgagtaat cattgccgcg cctaattttt ctaggtgttt tcaagtgtca tactgtttta   1320
gaaaattttg tatagaacaa atacgtatat cctgccatat catattcttt gcaatataca   1380
ccttgtacat ttggctatta taaatattac aatccattta atcataatca aaatttaatt   1440
tctgttacca cggggttgtc agtggagcat gccctgccgg ttctctataa tttatctttt   1500
tcacatgaga tatttttacc tcaaaaggta gtgatgctgt aataatatga ggctcccccc   1560
tttccttcgg aattgcattt aaatcattgg ggaacactaa gacaagacaa aggggccgtc   1620
cactcatgtg attttcaaca aaacagataa catgcggata cacactgata tattttcaaa   1680
ggaaagtctg actgatactt aagtgaagtg gtcctagtcg gtggcttagg tggactacag   1740
tgcaaagaat agaatttttc aaac                                           1764
```

<210> SEQ ID NO 13
<211> LENGTH: 154
<212> TYPE: PRT
<213> ORGANISM: Arabidopsis sp.

<400> SEQUENCE: 13

```
Met Leu Gln Asp Leu Tyr Val Asn Ile Gly Trp Pro Leu Tyr Arg Arg
  1               5                  10                  15

His Gly His Ala Phe Glu Ala Phe Lys Ile Leu Val Thr Asp Pro Asp
             20                  25                  30
```

-continued

Ser Val Leu Gly Pro Leu Thr Arg Glu Ile Lys Glu Val Gly Pro Asp
35 40 45

Gly Gln Glu Val Thr Lys Val Val Pro Ala Val Thr Glu Glu Val Lys
50 55 60

Asp Ala Leu Val Lys Asn Ile Arg Arg Arg Met Thr Pro Gln Pro Met
65 70 75 80

Lys Ile Arg Ala Asp Ile Glu Leu Lys Cys Phe Gln Phe Asp Gly Val
85 90 95

Val His Ile Lys Glu Ala Met Lys Asn Ala Glu Ala Ala Gly Asn Glu
100 105 110

Asp Cys Pro Val Lys Ile Lys Leu Val Ala Pro Pro Leu Tyr Val Leu
115 120 125

Thr Thr Gln Thr Leu Asp Lys Val Arg Gln Ser Ser Ile Leu His Tyr
130 135 140

Asp Leu Leu Gly Leu Val Ile Gly Ile Leu
145 150

<210> SEQ ID NO 14
<211> LENGTH: 1309
<212> TYPE: DNA
<213> ORGANISM: Arabidopsis sp.

<400> SEQUENCE: 14
ggaattcccg ggtcgaccca cgcgtccgaa accctaaatc tcaatcctcg acgctctcta 60
ctaagaaact caatcttact ttctctgtaa ttcgtagctt ccgaaatctt ttctcaagaa 120
tctcataacc atggcgaatc ctgctccgaa tctagaatgt cgtatgtacg aatcgagata 180
ccctgatgta gacatggcgg tgatgattca ggtgaagacc atcgctgaca tgggagctta 240
cgtatctctc cttgaataca acaacatcga aggaatgatc ctgttctccg agctctctcg 300
ccgtcggatt cgtagtatca gtagcttaat caaggtcggt cgtaccgagc ctgttatggt 360
ccttcgtgtc gatagagaga gaggttacat tgatctcagt aaacgtaggg ttagtgatga 420
ggacaaagag gcttgtgagg agaggtataa taagagcaag cttgttcact ctatcatgcg 480
tcatgttgct gagactgttg gtgtcgattt ggaggagcta tacgtaaaca tcggttggcc 540
attgtataag aagcatggac atgcttttga ggctttcaaa attgttgtca ctgatcctga 600
ttcagttttc gatgctctta cccgagaagt taaagaaact ggacctgatg gtgtggaggt 660
gaccaaagtt gtcccggctg tgtctgaaga attgaaagat gcatttttga aggacattag 720
gaggagaatg acaccacagc caatgaagat tcgtgctgat attgaattga agtgttttca 780
gtttgatgga gttctccaca tcaaggaagc catgaagaag gcagaggctg taggtactga 840
tgattgtcca gtcaaaatca agctcgttgc tccaccactt tatgtactca caactcacac 900
ccattacaag gaaaaaggaa tagtgactct gaataaagca attgaagcat gcattactgc 960
aattgaggaa cacaagggta aacttgtcgt taaagaaggt gctcgtgcgg tgagtgagcg 1020
tgatgacaaa ttgcttgctg agcacatggc taagcttaga atggataatg aagaaatgag 1080
tggtgatgag ggaagcgaag atgaagaaga cactggaatg ggagaagtcg atatcgatgg 1140
aggtagcggg ataattgaat gaacaaaagc aaaagcattg taactgctgt ttctgcttta 1200
gatcctacaa ttttgtttcc ctttgagcaa aaacagtatt ttttgtttga ccccaaacat 1260
ggttagtagt acaagcatct cttattcaaa aaaaaaaaaa aaaaaaaaa 1309

<210> SEQ ID NO 15

-continued

```
<211> LENGTH: 27
<212> TYPE: DNA
<213> ORGANISM: Triticum aestivum

<400> SEQUENCE: 15

tctccgagct cgcccgccgc cgcatcc                                          27
```

PLANT TRANSLATION METHODS AND COMPOSITIONS RELATED THERETO

FIELD OF THE INVENTION

The present invention relates to the field of plant molecular biology, in particular to translational control. The inventors herein disclose compositions and methods useful to alter plant gene translation, which methods enable genetic modification of numerous plant processes, such as inducible or constitutive responses to biotic and abiotic stress, or growth pattern adjustment.

BACKGROUND OF THE INVENTION

In yeasts and mammals, translational control is a reversible, rapid and highly discriminating mechanism of cell regulation. Merrick, W. C. and Hershey, J. W. B. (1996) *The pathway and mechanism of eukaryotic protein synthesis. IN: Translational Control.* Eds. Hershey, Mathews and Sonenberg. Cold Spring Harbor Press, NY. In these organisms, translational control is critically important in regulation of diverse physiological events including development, differentiation, response to biotic and abiotic stresses and apoptosis. In plants, however, little research has been done on translational control, and virtually nothing is known regarding the impact of translational regulation during plant growth. One of the best characterized translational control mechanisms in yeast and mammals involves the phosphorylation of eIF2α. Although the corresponding proteins have been found in plants, the physiological effects of in planta eIF2α phosphorylation are not understood.

Citation of the above documents is not intended as an admission that any of the foregoing is pertinent prior art. For example, in some instances above, the publication was less than one year before the filing date of this patent application. All statements as to the date or representation as to the contents of these documents is based on subjective characterization of information available to the applicant at the time of filing, and does not constitute an admission as to the accuracy of the dates or contents of these documents.

SUMMARY OF THE INVENTION

The present invention provides methods to affect gene translation in a plant, comprising altering the plant's inherent eIF2α activity. In one such embodiment, there are provided methods wherein the alteration has a result selected from the group consisting of: an increase in plant eIF2α protein amount during a time and in a tissue wherein plant eIF2α protein is inherently present at a lower amount; an increase in plant eIF2α protein amount during a time wherein plant eIF2α protein is inherently present at a lower amount; an increase in plant eIF2α protein amount in a tissue wherein plant eIF2α protein is inherently present at a lower amount; an increase in plant eIF2α protein amount in a tissue wherein plant eIF2α protein is inherently not present; an increase in plant eIF2α protein amount during a time wherein plant eIF2α protein is inherently not present; a decrease in plant eIF2α protein amount during a time and in a tissue wherein plant eIF2α protein is inherently present at a higher amount; a decrease in plant eIF2α protein amount during a time wherein plant eIF2α protein is inherently present at a higher amount; a decrease in plant eIF2α in a tissue wherein plant eIF2α is inherently present at a higher amount.

In a related aspect of the present invention, there are provided methods to increase translation in a plant, comprising increasing plant eIF2α activity to levels higher than inherently present in the plant. Those methods wherein said increase is by means of genetically-engineering the plant to comprise an expression construct comprising a plant eIF2α gene are preferred. More preferred are those methods wherein said expression construct is inducible. A most preferred aspect of these embodiments are those methods wherein said expression construct is induced by a condition selected from the group consisting of: pathogen attack; wounding; drought; hypoxia; light; high temperatures; and low temperatures. Methods wherein the plant is selected from the group consisting of: rice; soybean; maize; beet; tobacco; wheat; barley; poppy; rape; sunflower; alfalfa; sorghum; rose; carnation; gerbera; carrot; tomato; lettuce; chicory; pepper; melon; cabbage; canola; tulip; orchid and lilly; ornamental plant; turfgrass; horticultural tree; forest tree; conifer; banana tree; grass for hay; lettuce; fruit tree; and bush are preferred.

Also preferred are those methods wherein said plant eIF2α protein is encoded by a nucleic acid sequence selected from the group consisting of:

(a) a nucleic acid sequence which encodes an amino acid sequence which is more than 95% identical to an amino acid sequence selected from the group consisting of: SEQ ID NO 1; SEQ ID NO 3; SEQ ID NO 5; SEQ ID NO 7; SEQ ID NO 9; SEQ ID NO 11; and SEQ ID NO 13; wherein said identity can be determined using the DNAsis computer program and default parameters;

(b) a nucleic acid sequence which is more than 95% identical to a nucleic acid sequence selected from the group consisting of: SEQ ID NO 2; SEQ ID NO 4; SEQ ID NO 6; SEQ ID NO 8; SEQ ID NO 10; SEQ ID NO 12; and SEQ ID NO 14; wherein said identity can be determined using the DNAsis computer program and default parameters;

(c) a nucleic acid sequence which encodes an allelic variant of (a).

In other related aspects of the present invention are methods to decrease translation in a plant, comprising decreasing plant eIF2α activity to levels lower than inherently present in the plant. In this aspect, methods wherein said increase is by means of genetically-engineering the plant to impair inherent plant eIF2α genes are preferred.

In particular, those methods wherein said impairment is inducible are more preferred, especially with regard to those methods wherein said expression construct is induced by a condition selected from the group consisting of: pathogen attack; wounding; drought; hypoxia; light; high temperatures; and low temperatures. In this aspect, methods are also preferred wherein said plant is selected from the group consisting of: rice; soybean; maize; beet; tobacco; wheat; barley; poppy; rape; sunflower; alfalfa; sorghum; rose; carnation; gerbera; carrot; tomato; lettuce; chicory; pepper; melon; cabbage; canola; tulip; orchid and lilly; ornamental plant; turfgrass; horticultural tree; forest tree; conifer; banana tree; grass for hay; lettuce; fruit tree; and bush. Those wherein said plant eIF2α gene impaired is SEQ ID NO: 1 is particularly preferred.

Also provided are compositions of matter comprising a promoter operably linked to a plant eIF2α gene. These compositions of matter, wherein said promoter is a constitutive promoter are preferred. Also preferred are compositions of matter wherein said eIF2α gene is overexpressible and/or overexpressed. Plants comprising these compositions are also provided. Preferred plants are those selected from the group consisting of: rice; soybean; maize; beet; tobacco; wheat; barley; poppy; rape; sunflower; alfalfa; sorghum;

rose; carnation; gerbera; carrot; tomato; lettuce; chicory; pepper; melon; cabbage; canola; tulip; orchid; lilly; ornamental plant; turfgrass; horticultural tree; forest tree; conifer; banana tree; grass for hay; lettuce; fruit tree; and bush.

Also provided are knock-out constructs of the eIF2α gene which are capable of homologous recombination with the wild-type eIF2α gene, in particular plants comprising a knock-out construct herein.

DEFINITIONS

For the purposes of the present application, the following terms have the following meanings. All other terms have the meaning as generally recognized in the art.

"Allelic variant" is meant to refer to a gene that occurs at essentially the same locus (or loci) as the identified reference sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

"Inherent" means that genetic or phenotypic state of being which is present in a plant absent recombinant manipulation of eIF2α activity. In other words, a plant may be recombinantly altered, physiologically altered (via environmental manipulation) or otherwise altered, provided that the eIF2α gene present in that particular plant has not been recombinantly modified.

"Knock-out construct" means a DNA sequence which has been altered via any known means, for example, deletion, insertion, point mutation or rearrangement, so as to alter (including reduction in function e.g. hindering, and complete deletion) the function of the naturally-occurring gene product, but not so as to alter the ability of the DNA sequence to recombine with the naturally-occurring sequence.

"Operably-linked" means that the promoter is in a position relative to the gene such that the promoter has the ability to effect translation of the gene.

"Plant" means any whole plant or plant part, including, but not limited to: monocots and dicots; recombinant or non-recombinant plants; a plant cell culture; or a plant embryo, seed, leaf, flower, stem, root, fruit, etc.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
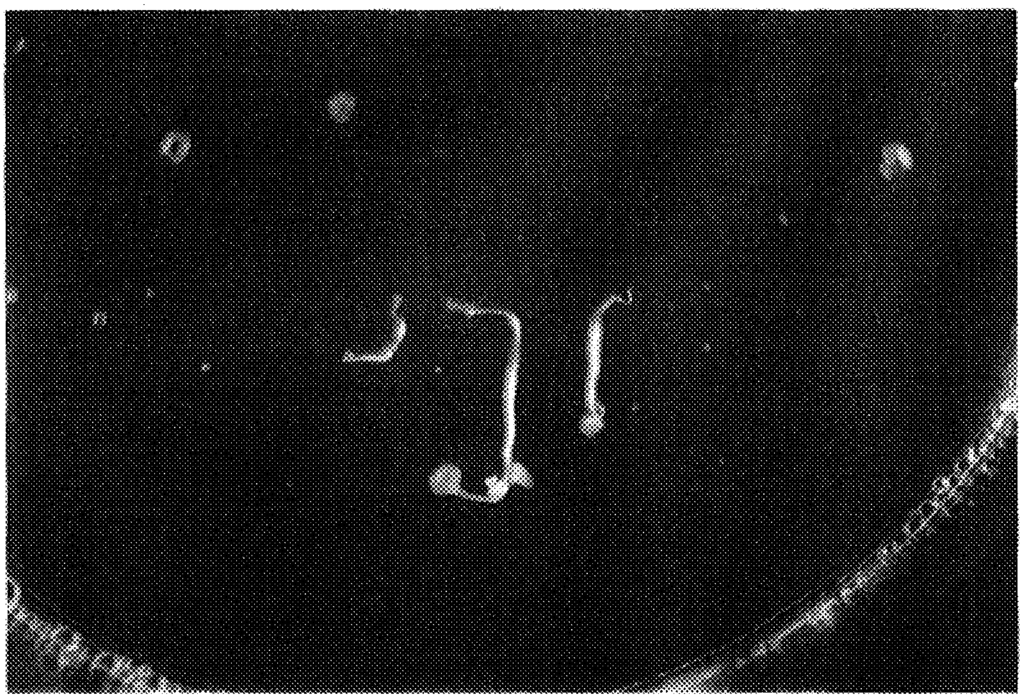
FIG. 1 Arabidopsis: Transformed with (from left to right). Vector only, eIF2α 51S-wild type, eIF2α 51A (stunted). These plants were vacuum infiltrated with Agrobacterium tumefaciens (strain LBA4404) containing plasmid pBI 121 with or without an insert (eIF2α). Seed was collected, sterilized and selected by plating on MS medium with kanamycin (50 ug/ml). The picture was taken 2 weeks post-gemination.
Figure 2:
FIG. 2 Tobacco: Leaf disks were transformed (50 disks/treatment) and planted on Shoot initiation medium (MS+0.5 mg/l BA), after 1 month shoots were transferred to medium without BA (media contained carbenicillin and epfotoxin and Kanamycin) for another 1 month.
Figure 3:
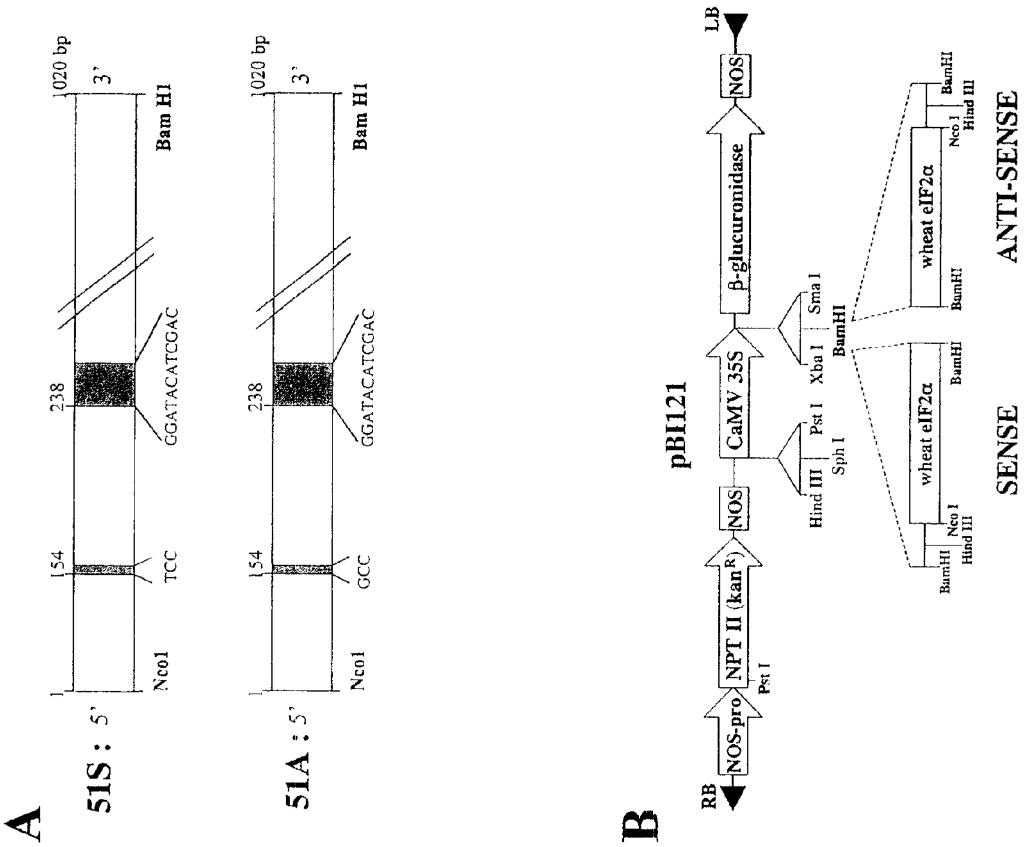
FIGS. 3A–3B A. Orientation and map of wheat eIF2alpha 51A & 51S sense and 51s antisense in pBI721. B. Original vector from Clonetech.

The present invention provides methods to affect gene translation in a plant, comprising altering the plant's inherent eIF2α activity. In one such embodiment, there are provided methods wherein the alteration has a result selected from the group consisting of: an increase in plant eIF2α protein amount during a time and in a tissue wherein plant eIF2α protein is inherently present at a lower amount; an increase in plant eIF2α protein amount during a time wherein plant eIF2α protein is inherently present at a lower amount; an increase in plant eIF2α protein amount in a tissue wherein plant eIF2α protein is inherently present at a lower amount; an increase in plant eIF2α protein amount in a tissue wherein plant eIF2α protein is inherently not present; an increase in plant eIF2α protein amount during a time wherein plant eIF2α protein is inherently not present; a decrease in plant eIF2α protein amount during a time and in a tissue wherein plant eIF2α protein is inherently present at a higher amount; a decrease in plant eIF2α protein amount during a time wherein plant eIF2α protein is inherently present at a higher amount; a decrease in plant eIF2α in a tissue wherein plant eIF2α is inherently present at a higher amount.

In a related aspect of the present invention, there are provided methods to increase translation in a plant, comprising increasing plant eIF2α activity to levels higher than inherently present in the plant. Those methods wherein said increase is by means of genetically-engineering the plant to comprise an expression construct comprising a plant eIF2α gene are preferred. More preferred are those methods wherein said expression construct is inducible. A most preferred aspect of these embodiments are those methods wherein said expression construct is induced by a condition selected from the group consisting of: pathogen attack; wounding; drought; hypoxia; light; high temperatures; and low temperatures. Methods wherein the plant is selected from the group consisting of: rice; soybean; maize; beet; tobacco; wheat; barley; poppy; rape; sunflower; alfalfa; sorghum; rose; carnation; gerbera; carrot; tomato; lettuce; chicory; pepper; melon; cabbage; canola; tulip; orchid and lilly; ornamental plant; turfgrass; horticultural tree; forest tree; conifer; banana tree; grass for hay; lettuce; fruit tree; and bush are preferred. Also preferred are those methods wherein said plant eIF2α gene is SEQ ID NO: 1. However, any eIF2α gene can be used in the present embodiments, including: Human: J02645; NM004094; zebrafish: AF257517; Rat: J02646; Yeast: YJR007W; and Arabidopsis: AC007020 (eIF2 is in this chromosome site) can be used. The citations are from the NIH BLAST database at http://www.ncbi.nlm.nih.gov/, where the sequences can be found.

An amino scid sequence of the alpha subunit of wheat eukaryotic initiation factor 2 is:
MANLECRMYEPRFPEVDAAVMIQVKHIADM GAYVSLLEYNNVEGMILFSELSRRR IRSISS-LIKVGRQEPAIVLRVDRDKGYIDLSKRRVSEEEAR SCEDKYNKSKLVHSIM RHVAETLEIDLEPIYQRIGW-PLYRKYGHAFEAFKLIVADPDAILDVLTYEERETGPD GQEVTKVVPAVTPEIKETLVQNIRRRMTPQP LKIRADVEMKCFQFDGVLHIKQAM RKAEAAGNT-NCPVKIKLVAPPPLYVLTTQTLDKDQGISVLTDAV KACTAEIEKHK GKLVVKEAPRAVSERED-KLLNAQLDTLVEQNAEVAGDDDSEDEEDTG MGDIDLT NSGVHAD (SEQ ID NO 1)

A nucleic acid sequence which contains the coding region of the alpha subunit of wheat eukaryotic initiation factor 2 is:

CTTCTTCTTGCGCCCGCTCGGCAGAAAT-TGTACACGTTTTTCATTTCGAAAAGTC-CAAATTGCCCATTTTTTGGCCATAGAC-CACAGACTTTAAC ATGGCCCTGACGTCGCGCTTCTACAAC-GAGCGGTATCCGGAGATCGAGGAT-GTCGTTATGGTG AACGTGCTGTCCATCGC-CGAGATGGGCGCCTACGTTCATCTGCTTGAGTACA ACAACATCGAG GGCATGATCCTGCTGTCGGAGCT-GTCCCGCCGGCGCATCCGCTCCATCAA-CAAGCTGATTCGT GTCGGCAAGACCGAACCGGTG-GTGGTTATCCGTGTTGACAAGGAGAAGGGCTACA TCGATCTG TCGAAGCGTCGCGTTTCGCCCGAAGAT-GTCGAGAAGTGCACCGAGCGCT-TCGCTAAGGCCAAG GCCATCAACTCACTGCTC-CGCCATGTCGCCGACATACTCGGCTTCGAGGGCAA CGAGAAGCTG GAAGATCTCTACCAGAAGACCGC-CTGGCACTTCGAGAAGAAGTACAACAA-CAAGACGGTCGC CTACGACATCTTCAAGCAATCG-GTCACCGATCCCACCGTCTTCGATGAGTGCAACCT GGAACC GGAGACCAAGGAGGTCCTGTTGAGCAA-CATCAAGCGGAAGCTGGTCTCGCCCACT-GTCAAGAT CCGTGCGGACATCGAGTGCTCCTGC-TACGGTTACGAGGGCATCGACGCTGTCAAGGCATC GCT CACCAAGGGCCTGGAGCTGAGCACCGAG-GAGCTGCCCATTCGCATCAACCTGATAGCACCGC CACTCTATGTAATGACCACATCCACTAC-CAAGAAGACAGACGGTTTAAAGGCTCTG-GAGGTGG CCATTGAGCACATTCGCGCCAAGAC-CAGCGAGTACGATGGAGAGTTCAAGGTGATCATGG CAC CCAAACTGGTTACGGCCATCGACGAG-GCGGATCTGGCCAGACGCCTG-GAGCGCGCTGAGGCC GAGAACGCCCAGGTG-GCTGGCGACGATGACGAGGAGGATGGCGCCGACC AGGAGGGCATGCA GTTCGATCCAGAGAAGGAGT-TCAACCACAAGG-GATCGGGGGCGGGTCGTGCGAACGAGGAGG ATGAGGAGGAGGAAGAGGATTAGCG-TAGCCACAGCATCAGACACAACTATAG-CAACTGTAACA AACAATTAAAGGAGTTTTG-CAAAAATC (SEQ ID NO 2)

Human: J02645:

MPGLSCRFYQHKFPEVEDVVMVNVRSI-AEMGAYVSLLEYNNIEGMILLSELSRRR IRSINKLIRI-GRNECVVVIRVDKEKGYIDL-SKRRVSPEEAIKCEDKFTKSKTVYSILR HVAEVLEYTKDEQLESLFQRTAWVFD-DKYKRPGYGAYDAFKHAVSDPSILDSLD LNEDER-EVLINNINRRLTPQAVKIRADIEVA-CYGYEGIDAVKEALRAGLNCSTEN MPIKINLIAPPRYVMTTTTLERTEGLSV-LSQAMAVIKEKIEEKRGVFNVQMEPK VVTDTDETE-LARQMERLERENAEVDGDDDAEEMEAKAED (SEQ ID NO 3)

1 gtgcgggaat cacacacata cctcagaatg ccgggtctaa gttgtagatt ttatcaacac 61 aaatcctg aggtggaaga tgtagtgatg gtgaatgtca gatccattgc tgaaatgggg 121 gcttatgtca gcttgctgga atacaacaac attgaaggca tgattcttct tagtgaatta 181 tccagaaggc gtatccgttc tatcaacaaa ctcatccgaa ttggcaggaa tgagtgtgtg 241 gttgtcatta gggtggacaa agaaaaagga tatattgatt tgtcaaaaag aagagtttct 301 ccagaggaag caatcaaatg tgaagacaaa ttcacaaaat ccaaaactgt ttatagcatt 361 cttcgtcatg ttgctgaggt gttagaatac accaaggatg agcagctgga aagcctattc 421 cagaggactg cctgggtctt tgatgacaag tacaagagac ctggatatgg tgcctatgat 481 gcatttaagc atgcagtctc agacccatct attttggata gtttagattt gaatgaagat 541 gaacgggaag tactcattaa taatattaat aggcgcttga ccccacaggc tgtcaaaatt 601 cgagcagata ttgaagtggc ttgttatggt tatgaaggca ttgatgctgt aaaagaagcc 661 ctaagagcag gtttgaattg ttctacagaa aacatgccca ttaagattaa tctaatagct 721 cctcctcggt atgtaatgac tacgacaacc ctggagagaa cagaaggcct ttctgtcctc 781 agtcaagcta tggctgttat caaagagaag attgaggaaa agagggggtgt gttcaatgtt 841 caaatggagc ccaaagtggt cacagataca gatgagactg aacttgc-gag gcagatggag 901 aggcttgaaa gagaaaatgc cgaagtggat ggagatgatg atgca-gaaga aatggaagcc 961 aaagctgaag attaactttg tgggaaacag agtccaattt aaggaacaca gagcagcgct 1021 tcctggctgt aaatcctaga cttgaaagtt ttccagtatt gaaaacttca aagctgaata 1081 ttttttattt ctaagtattt aaatgttcta acagatcaga acatgaaatg ccctcctaaa 1141 tgtcagctgt tgtcacacag tagctccaac actttgagca tttttaaggg agtggcctca 1201 tttcactaga gacaaatctt taagaatagt tctaaaattg ggcttgtgat ttccatttct 1261 gatgtctcca gattggcacc cctttctagt tcaatgcctc acgagatttg ccaggggcat 1321 ccaaggcaaa caatcccaat ctttctatat aaaatgtatt caagcaaaca tcaaataaat 1381 ttctgggata ttt (SEQ ID NO 4)

Human NM004094:

MPGLSCRFYQHKFPEVEDVVMVNVRSI-AEMGAYVSLLEYNNIEGMILLSELSRRR IRSINKLIRI-GRNECVVVIRVDKEKGYIDL-SKRRVSPEEAIKCEDKFTKSKTVYSILR HVAEVLEYTKDEQLESLFQRTAWVFD-DKYKRPGYGAYDAFKHAVSDPSILDSLD LNEDER-EVLINNINRRLTPQAVKIRADIEVA-CYGYEGIDAVKEALRAGLNCSTEN MPIKINLIAPPRYVMTTTTLERTEGLSV-LSQAMAVIKEKIEEKRGVFNVQMEPKV VTDTDETE-LARQMERLERENAEVDGDDDAEEMEAKAED (SEQ ID NO 5)

1 gtgcgggaat cacacacata cctcagaatg ccgggtctaa gttgtagatt ttatcaacac 61 aaatttcctg aggtggaaga tgtagtgatg gtgaatgtca gatccattgc tgaaatgggg 121 gcttatgtca gcttgctgga atacaacaac attgaaggca tgattcttct tagtgaatta 181 tccagaaggc gtatccgttc tatcaacaaa ctcatccgaa ttggcaggaa tgagtgtgtg 241 gttgtcatta gggtggacaa agaaaaagga tatattgatt tgtcaaaaag aagagtttct 301 ccagaggaag caatcaaatg tgaagacaaa ttcacaaaat ccaaaactgt ttatagcatt 361 cttcgtcatg ttgctgaggt gttagaatac accaaggatg agcagctgga aagcctattc 421 cagaggactg cctgggtctt tgatgacaag tacaagagac ctggatatgg tgcctatgat 481 gcatttaagc atgcagtctc agacccatct attttggata gtttagattt gaatgaagat
541 gaacgggaag tactcattaa taatattaat aggcgcttga ccccacaggc tgtcaaaatt
601 cgagcagata ttgaagtggc ttgttatggt tatgaaggca ttgatgctgt aaaagaagcc
661 ctaagagcag gtttgaattg ttctacagaa aacatgccca ttaagattaa tctaatagct
721 cctcctcggt atgtaatgac tacgacaacc ctggagagaa cagaaggcct ttctgtcctc
781 agtcaagcta tggctgttat caaagagaag attgaggaaa agagggggtgt gttcaatgtt
841 caaatggagc ccaaagtggt cacagataca gatgagactg aacttgc-gag gcagatggag
901 aggcttgaaa gagaaaatgc cgaagtggat ggagatgatg atgca-gaaga aatggaagcc
961 aaagctgaag attaactttg tgggaaacag agtccaattt aaggaacaca gagcagcgct
1021 tcctggctgt aaatcctaga cttgaaagtt ttccagtatt gaaaacttca aagctgaata
1081 tttttatttt ctaagtattt aaatgttcta acagatcaga acatgaaatg ccctcctaaa
1141 tgtcagctgt tgtcacacag tagctccaac actttgagca tttttaaggg agtggcctca
1201 tttcactaga gacaaatctt taagaatagt tctaaaattg ggcttgtgat ttccatttct
1261 gatgtctcca gattggcacc cctttctagt tcaatgcctc acgagatttg ccaggggcat
1321 ccaaggcaaa caatcccaat ctttctatat aaaatgtatt caagcaaaca tcaaataaat
1381 ttctgggata ttt (SEQ ID NO 6)

zebrafish AF257517:

MPGLSCRFYQHRFPEVEDVVMVNVRSI-
AEMGAYVSLLEYNNIEGMILLSELSRRR IRSINKLIRI-
GRNECVVVIRVDKEKGYIDL-
SKRRVSPEEAIKCEDKFTKSKTVYSILR
HfVAEVLEYTKDEQLESLFQRTAWVFDE-
KYKKPGYGAYDVFKQAVSDPAILDGL DLTEEERNV-
LIDNINRRLTPQAVKIRADIEVA-
CYGYEGIDAVKEALRAGLNCSTE
AMPIKINLIAPPRYVMTTTTLERTEGLS-
VLNQAMAAIKERIEEKRGVFNVQMEP KVVTDTDE-
TELQRQLERLERENAEVDGDDDAEEMEAKTED (SEQ ID NO 7)

1 atgccgggtc taagctgtag attttaccag caccgcttcc ccgaggtgga ggacgtggtg
61 atggtgaacg tgcgctcgat cgctgagatg ggagcgtatg tgagtctgct ggagtacaac
121 aacatcgagg gcatgatcct gctgagcgaa ctgtcccgca gacg-catccg ctccatcaac
181 aaactcatcc gcatcggacg caacgagtgt gtggtggtca tcagggtgga caaggagaag
241 ggttacattg atctgtccaa gagaagagtg tctccagaag aagccatcaa atgcgaggat
301 aaattcacca aatctaaaac cgtgtacagt attttgcggc acgtggctga ggtgttggag
361 tacaccaaag acgagcagct ggagagtttg ttccagagaa ccgcttgggt ttttgatgag
421 aaatacaaga agcctggata cggggcctac gacgtcttta aacaagctgt gtctgatcct
481 gccattctgg atggtttgga tctgactgag gaagagagaa acgtgctcat cgacaacatc
541 aacaggcgac tcacaccaca ggccgtcaaa ataagagctg acat-tgaggt ggcgtgttat
601 ggatatgaag gcatcgatgc agtgaaggag gctctgaggg caggact-caa ttgctccact
661 gaagccatgc ctatcaagat caacctgatc gcgccgccgc ggtacgtcat gaccaccaca
721 acactggagc gaacagaagg cctgtcagtg ctcaaccagg ccatggc-cgc aattaaagag
781 cggatcgagg agaagcgagg agtcttcaat gtgcagatgg agc-ccaaggt ggtgacggac
841 acagacgaga cggaactgca gcggcagctc gagcgtctgg agc-gagaaaa cgcagaagtg
901 gacggagacg acgatgcaga agagatggag gccaaaactg aggac-tag (SEQ ID NO 8)

Rat: J02646:

MPGLSCRFYQHKFPEVEDVVMVNVRSI-
AEMGAYVSLLEYNNIEGMILLSELSRRR IRSINKLIRI-
GRNECVVVIRVDKEKGYIDLSKRRVSPEEAIKCEDKF
TKSKTVYSILRHVAEVLEYTKDEQLE-
SLFQRTAWVFDDKYKRPGYGAYDAFKH AVSDP-
SILDSLDLNEDEREVLINNINRRLT-
PQAVKIRADIEVACYGYEGIDAVKEA
LRAGLNCSTETMPIKINLIAP-
PRYVMTTTTLERTEGLSVLNQAMAVIKEKIEEKR
GVFNVQMEPKVVTDTDETELARQLER-
LERENAEVDGDDDAEEMEAKAED (SEQ ID NO 9)

1 gttcgggatt cacacataca cttcagaatg ccgggtctaa gttgtagatt ttat-caacac
61 aaatttcctg aggtcgaaga tgtagtgatg gtgaatgtaa gatccattgc tgaaatgggg
121 gcctatgtca gcttgttgga atataataac attgaaggca tgattcttct tagtgaatta
181 tccagacgac gtatccgttc tataaacaaa ctgatccgaa ttggcagaaa tgaatgtgta
241 gttgtcatta gagtggataa agaaaaagga tatatagatt tgtcaaaaag aagagtttct
301 ccagaggaag caatcaaatg tgaagacaaa ttcacaaaat ccaaaactgt ttatagcatt
361 cttcgccatg ttgctgaggt attagagtat accaaggatg agcagctgga aagcctattc
421 cagaggactg cctgggtctt tgatgacaag tacaagagac ctggatatgg tgcctatgat
481 gcctttaagc atgcagtctc agacccatct atcttggata gtttagattt gaatgaagat
541 gaaagagaag tactcattaa caatatcaat aggcgtttga ccccacaagc tgtcaagatt
601 cgagcagata ttgaggtagc ttgctatggt tacgaaggca ttgatgctgt aaaagaagcc
661 ctgagagcag gtttgaattg ttctacagaa accatgccca tcaagattaa tctaatagct
721 ccacccaggt atgtgatgac aacaacgacc ctagagagga cagaag-gact ctctgttctc
781 aatcaggcta tggcagtcat caaagaaaag attgaggaga agaggg-gagt gttcaatgtt
841 cagatggagc ccaaagtggt tacagataca gatgagactg aacttgcaag gcagctggaa
901 cggcttgaga gagaaaatgc agaagtggat ggagatgatg atgca-gaaga aatggaagcc
961 aaagctgaag attaaccttt tggaaaacag tccaatttaa ggagtacgaa gcagcccttt
1021 ctggctgtaa accctagact tgaaagtttt ccagtattga aaacttcaaa gctgaatatt
1081 tttatttcca agtatttaag tattcgacaa gccagaatct aaatgccctc cttcatgtca
1141 gctgttttca catagtggct ctaacacctc aagcgttttt aagggagtgg cgatttga
1201 ccagagacaa atgttaaacc gcagtcctaa aattgggctt gcggttttca tttctgatgt
1261 ctctggattg gcacccttat ggtttagaga attaccaggg gctccagaca ccaacaatcc 1321 caacctttct atataaaatg tactcaagca aacatcaaat aaatttctgg gatattt (SEQ ID NO 10)

Yeast: YJR007W:

MSTSHCRFYENKYPEIDDIVMVNVQQI-AEMGAYVKLLEYDNIEGMILLSELSRRR IRSIQK-LIRVGKNDVAVVLRVDKEKGYIDL-SKRRVSSEDIIKCEEKYQKSKTVHSIL RYCAEKFQIPLEELYKTIAWPLSRKF-GHAYEAFKLSIIDETVWEGIEPPSKDVLDEL KNY-ISKRLTPQAVKIRADVEVSCFSYEGID-AIKDALKSAEDMSTEQMQVKVKLV AAPLYVLTTQALDKQKGIEQLESAIE-KITEVITKYGGVCNITMPPKAVTATEDAE LQALL-ESKELDNRSDSEDDEDESDDE (SEQ ID NO 11)

1 ataaaacaag gaataatttc cacatagata tgcaattaag ttttatatgt aaaagtgagc 61 attcatcgtt cagctcaaaa tacgtttctt gtcacagctg gtagaaaaac tatgagcgtt 121 ttttcttacc cgcagtcgga gaaaaatttt ttcttcgaag aggcgaaaaa gagaagaaga 181 gaaagcacaa atctgatgaa atagtagtat aaaatcgcat ttacaaattt tcaaccattg 241 tttatttcct aggtcattaa agagtaaagt gcaatctgtt tactaatcag tttttgtctt 301 catatttttg tgtcttttct gctgcctcac gcaccttcta taatacacca aataatgtcc 361 acttctcatt gcagatttta tgaaaacaaa tacccagaaa ttgacgatat cgtcatggtt 421 aacgtccagc agattgctga aatgggtgct tatgttaaat tgttagaata tgacaacatt 481 gaaggtatga ttctactaag tgaattgtcc cgtagacgta ttaggtcaat ccaaaaaatta 541 attcgtgttg gtaaaaatga tgtcgccgtt gttcttcgtg tcgacaaaga aaaaggtat 601 attgatttgt ccaaacgtcg tgtttcttct gaagatatca ttaaatgtga agaaaaatac 661 caaaaatcta agactgttca ttccatttta agatactgtg ccgaaaaatt ccaaatccct 721 ttggaagaac tatataagac cattgcttgg ccattaagtc gaaaatttgg tcacgcttac 781 gaagctttca aactatccat cattgacgaa actgtttggg aaggtattga accgccatca 841 aaagatgttt tagatgaatt aaagaactat atctccaaga gattaacacc acaagctgta 901 aagattagag ccgatgttga agtgtcttgt tttagttacg aaggtatcga tgccattaaa 961 gacgcattaa aatcagctga agacatgtcc acagaacaaa tgcaagttaa agttaaatta 1021 gtcgccgccc cattatatgt tttgaccacc caagccttgg ataagcaaaa aggtattgaa 1081 caactggaaa gcgctattga aaaaattaca gaggttatta caaaatacgg cggtgtttgc 1141 aacattacca tgccaccaaa ggctgtcact gctactgaag acgctgagtt acaagctcta 1201 ttagaaagca aagaattaga taatagatct gactctgaag acgat-gagga tgagtcagac 1261 gacgagtaat cattgccgcg cctaattttt ctaggtgttt tcaagtgtca tactgtttta 1321 gaaaattttg tatagaacaa atacgtatat cctgccatat catattcttt gcaatataca 1381 ccttgtacat ttggctatta taaatattac aatccattta atcataatca aaatttaatt 1441 tctgttacca cggggttgtc agtggagcat gccctgccgg ttctctataa tttatctttt 1501 tcacatgaga tatttttacc tcaaaaggta gtgatgctgt aataatatga ggctcccccc 1561 tttccttcgg aattgcattt aaatcanggg ggaacactaa gacaagacaa agggggccgtc 1621 cactcatgtg attttcaaca aaacagataa catgcggata cacactgata tattttcaaa 1681 ggaaagtctg actgatactt aagtgaagtg gtcctagtcg gtggcttagg tggactacag 1741 tgcaaagaat agaatttttc aaac (SEQ ID NO 12)

Arabidopsis: AC007020 (eIF2 is in this chromosome site)

MLQDLYVNIGWPLYRRHGHAFEAFKIL-VTDPDSVLGPLTREIKEVGPDGQEVTK VVPAV-TEEVKDALVKNIRRRMTPQPMKIRADI-ELKCFQFDGVVHIKEAMKNAE AAGNEDCPVKIKLVAPPLYVLTTQTLD-KVRQSSILHYDLLGLVIGIL (SEQ ID NO 13)

GGAATTCCCGGGTCGACCCACGCGTC-CGAAACCCTAAATCTCAATCCTC-GACGCTCTCTACTAAGAAACTCAAT CTTACTTTCTCTGTAATTCGTAGCTTC-CGAAATCTTTTCTCAAGAATCTCATAAC-CATGGCGAATCCTGCTCCGAA TCTAGAATGTCG-TATGTACGAATCGAGATACCCTGATGTAGACATGGC GGTGATGATTCAGGTGAAGACCATCGC TGA-CATGGGAGCTTACGTATCTCTCCT-TGAATACAACAACATCGAAGGAATGATC-CTGTTGTCCGAGCTCTCTCG CCGTCGGATTCGTAGTATCAGTAGCT-TAATCAAGGTCGGTCGTACCGAGCCTGT-TATGGTCCTTCGTGTCGATAG AGAGAGAGGTTA-CATTGATCTCAGTAAACGTAGGGTTAGTGATGAGGA CAAAGAGGCTTGTGAGGAGAGGTATA ATAAGAG-CAAGCTTGTTCACTCTATCATGCGTCAT-GTTGCTGAGACTGTTGGTGTCGATTTG-GAGGAGCTATACGT AAACATCGGTTGGCCATTGTATAAGAAG-CATGGACATGCTTTTGAGGCTTCAAAAT-TGTTGTCACTGATCCTGAT TCAGTTTTCGATGCTCT-TACCCGAGAAGTTAAAGAAACTGGACCTGATGGTG TGGAGGTGACCAAAGTTGTCCCG GCTGTGTCT-GAAGAATTGAAAGATGCATTTGAAGGA-CATTAGGAGGAGAATGACACCACAGC-CAATGAAGATT CGTGCTGATATTGAATTGAAGT-GTTTTCAGTTTGATGGAGTTCTCCACAT-CAAGGAAGCCATGAAGAAGGCAGAG GCTGTAGG-TACTGATGATTGTCCAGTCAAAATCAAGCTCGTTG CTCCACCACTTTGTACTCACAACTCACACC CATTA-CAAGGAAAAAGGAATAGTGACTCT-GAATAAAGCAATTGAAGCATGCATTACT-GCAATTGAGGAACACAA GGGTAAACTTGTCGTTAAAGAAGGT-GCTCGTGCGGTGAGTGAGCGTGATGA-CAAATTGCTTGCTGAGCACATGGC TAAGCTTA-GAATGGATAATGAAGAAATGAGTGGTGATGAGGGA AGCGAAGATGAAGAAGACACTGGAATGGGAG AAGTCGATATCGATGGAGGTAGCGG-GATAATTGAATGAACAAAAGCAAAAG-CATTGTAACTGTCTTTCTGCTTT AGATCCTA-CAATTTTGTTTCCCTTTGAGCAAAAACAGTATTTTT TGTTTGACCCCAAACATGGTTAGTAGTACAAG CATCTCTTATTCAAAAAAAAAAAAAAAAAAAAAA (SEQ ID NO 14)

In other related aspects of the present invention are methods to decrease translation in a plant, comprising decreasing plant eIF2α activity to levels lower than inherently present in the plant. In this aspect, methods wherein said increase is by means of genetically-engineering the plant to impair inherent plant eIF2α genes are preferred.

In particular, those methods wherein said impairment is inducible are more preferred, especially with regard to those methods wherein said expression construct is induced by a condition selected from the group consisting of: pathogen attack; wounding; drought; hypoxia; light; high temperatures; and low temperatures. In this aspect, methods are also preferred wherein said plant is selected from the group consisting of: rice; soybean; maize; beet; tobacco; wheat; barley; poppy; rape; sunflower; alfalfa; sorghum; rose; carnation; gerbera; carrot; tomato; lettuce; chicory; pepper; melon; cabbage; canola; tulip; orchid and lilly; ornamental plant; turfgrass; horticultural tree; forest tree; conifer; banana tree; grass for hay; lettuce; fruit tree; and bush.

Also preferred are those methods wherein said plant eIF2α protein is encoded by a nucleic acid sequence selected from the group consisting of:

(a) a nucleic acid sequence which encodes an amino acid sequence which is more than 95% identical to an amino acid sequence selected from the group consisting of: SEQ ID NO 1; SEQ ID NO 3; SEQ ID NO 5; SEQ ID NO 7; SEQ ID NO 9; SEQ ID NO 11; and SEQ ID NO 13; wherein said identity can be determined using the DNAsis computer program and default parameters;

(b) a nucleic acid sequence which is more than 95% identical to a nucleic acid sequence selected from the group consisting of: SEQ ID NO 2; SEQ ID NO 4; SEQ ID NO 6; SEQ ID NO 8; SEQ ID NO 10; SEQ ID NO 12; and SEQ ID NO 14; wherein said identity can be determined using the DNAsis computer program and default parameters;

(c) a nucleic acid sequence which encodes an allelic variant of (a).

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

In other related aspects of the present invention are compositions of matter comprising a promoter capable of causing expression of plant eIF2α, and the plant eIF2α gene. Plants comprising those compositions are preferred.

Also provided are compositions of matter comprising a promoter operably linked to a plant eIF2α gene. These compositions of matter, wherein said promoter is a constitutive promoter are preferred. Also preferred are compositions of matter wherein said eIF2α gene is overexpressible and/or overexpressed. Plants comprising these compositions are also provided. Preferred plants are those selected from the group consisting of: rice; soybean; maize; beet; tobacco; wheat; barley; poppy; rape; sunflower; alfalfa; sorghum; rose; carnation; gerbera; carrot; tomato; lettuce; chicory; pepper; melon; cabbage; canola; tulip; orchid; lilly; ornamental plant; turfgrass; horticultural tree; forest tree; conifer; banana tree; grass for hay; lettuce; fruit tree; and bush.

Also provided are knock-out constructs of the eIF2α gene which are capable of homologous recombination with the wild-type eIF2α gene, in particular plants comprising a knock-out construct herein.

Moreover, one commercially significant use of the present invention is in the construction of "knockout mutants" of eIF2α, for design and construction of translationally-modified plants. In other words, the present invention is informative to those skilled in the art as to their usefulness in making the naturally-occuring gene inactive. For example, the eIF2α sequences can be mutated by any means, i.e., deletion, insertion, point mutation, rearrangement, etc, so long as the mutated version retains the ability to recombine. The mutated version of the gene is then introduced into cells of a plant line via routine methods (ie. biolistic processes, lambda phage transformation, etc.). Translationally-altered mutants of the preferred line would then be selected and propagated. These "knockout" mutant embryos, seeds and plants are within the scope of the present invention, as are the knockout constructs, ie. sequences and vectors. Ideally, the mutant would not have complete arrest of translation, but rather localized (ie. flower) arrest, or general or localized impairment (resulting in, for example, a dwarf variety).

The "knockout mutants" are simply those which result in a non-phosphorylatable eIF2a alleles. They may be a result of an alanine or any other amino acid codon other than serine or threonine for position 51 of the protein. A mutant which encodes an aspartic acid or alanine at position 51 is particularly preferred, as are methods which use them.

For example, the following seeds, embryos or plants transformed with knockout constructs are considered within the present invention: soybean, maize, beet, tobacco, wheat, barley, poppy, rape, sunflower, alfalfa, sorghum, rose, carnation, gerbera, carrot, tomato, lettuce, chicory, pepper, melon and cabbage. However, various ornamentals (flowers etc), turfgrass and horticultural trees such as banana are particularly preferred, since reduced height would be an advantage. Of course, those in the art recognize that any seed, embryo or plant transformed with knockout constructs which are useful for producing plants for biomass are within the scope of the present invention.

Transformation of cells with the compounds of the present invention can be accomplished according to known procedures. For example, infective, vector-containing bacterial strains (such as *Agrobacterium rhizogenes* and *Agrobacterium tumefaciens*) may be used for transformation. Zambryski, 43 *Ann. Rev. Pl. Physiol. Pl. Mol. Biol.* 465 (1992). The following procedures are also well-known: Pollen-tube transformation [Zhonxun et al., 6 *Plant Molec. Bio.* 165 (1988)]; direct transformation of germinating seeds [Toepfer et al., 1 *Plant Cell* 133 (1989)]; polyethylene glycol or electroporation tranformation [Christou et al., 84 *Proc. Nat. Acad. Sci.* 3662 (1987)]; and biolistic processes [Yang & Cristou, *Particle Bombardment Technology for Gene Transfer* (1994)]. The transformed cells are also within the scope of the present invention.

The transformed cells may be induced to form transformed plants via organogenesis or embryogenesis, according to the procedures of Dixon *Plant Cell Culture: A Practical Approach* (IRL Press, Oxford 1987).

Therefore, also provided are methods for constructing sequences with the ability to knockout the above sequences, comprising one of the following techniques: inserting a foreign piece of DNA into a plant eIF2α gene; deleting a piece of DNA from one of a plant eIF2α gene; or creating a mutation such that the plant eIF2α gene activity is reduced or eliminated.

Also provided are antisense constructs and methods to inhibit mRNA transcripts of eIF2α, so as to either eliminate or reduce the amount of gene product. The procedures for antisense inhibition for mRNA are described in U.S. Pat. No. 5,554,743, which patent is expressly incorporated by reference into this application.

Also provided in the present invention are methods to improve seed germination, comprising expressing or overexpressing the eIF2α gene described herein [i.e., Cucumis Speices; Yim and Bradford, 114(3) Plant Physiology 289, abstract 1506 (1997)]. The seeds can then be germinated according to traditional methods. Overexpression can be as skill of the art, in particular, according to the procedures described in U.S. Pat. No. 5,477,001.

Lastly, the present invention includes methods to alter the naturally-occurring expression pattern of a plant eIF2α gene so as to either delay or prematurely encourage translation.

Since disease resistance is one characteristic conferred to a plant by the expression of a plant eIF2α gene, an ideal method would be to activate the gene upon threatened or actual disease, and have the gene constitutively expressed thereafter.

In particular, in order to practice the altered expression pattern aspect of the present invention, one would have to construct a vector which provided for either an early or late promoter in conjunction with the present sequences. For instance, the following promoters would be useful in early expression of the present sequences:

Ogs4B (Tsuchiya et al., 36 *Plant Cell Physiology* 487 (1994)
TA29 (Koltunow et al, 2 *Plant Cell* 1201 (1990)
A3 & A9 (Paul et al., 19 *Plant Molecular Biology* 611 (1992)

In order to then constitutively express the sequences described above, the construct optionally contains, for example, a 35S promoter.

A variety of procedures known in the art may be used to molecularly clone the present nucleic acids. These methods include, but is not limited to complementation for function following the construction of a genomic DNA library in an appropriate vector system. Another method is to screen a genomic DNA library constructed in a bacteriophage or plasmid shuttle vector with a labeled oligonucleotide probe designed from the amino acid sequence of the gene. An additional method consists of screening genomic DNA libraries constructed in a bacteriophage or plasmid shuttle vector with a partial DNA encoding the gene. This partial DNA is obtained by specific PCR amplification of the gene DNA fragments through the design of degenerate oligonucleotide primers from the amino acid sequence of the purified gene product or by using another member of the gene family as a probe. Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993) describe these procedures.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ. (Murray et al., 17 *Nucl Acids Res* 477 (1989). Thus, the maize preferred codon for a particular amino acid may be derived from known gene sequences from maize. Maize codon usage for 28 genes from maize plants are listed in Table 4 of Murray et al., supra.

The cloned nucleic acids may be expressed through the methods described in the examples or methods known in the art. The DNA can be recombinantly expressed by molecular cloning into an expression vector containing a suitable promoter and other appropriate transcription regulatory elements, and transferred into prokaryotic or eukaryotic host cells to produce recombinant gene product. Techniques for such manipulations are fully described in Sambrook, J., et al, supra. Expression vectors can be used to express genes in a variety of hosts such as bacteria, bluegreen algae, plant cells, insect cells, fungal cells and animal cells. Expression vectors may include, but are not limited to, cloning vectors, modified cloning vectors, specifically designed plasmids or viruses.

Vectors which comprise the nucleic acid compounds are within the scope of the present invention, as are plants transformed with the above nucleic acid compounds. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.).

Preferred vectors are those which are capable of transferring the sequences disclosed herein into plant cells or plant parts. Expression vectors are preferred, with expression vectors comprising an inducible promoter operably linked to the nucleic acid compound being more preferred. "Inducible" promoters typically direct expression of a polynucleotide in a specific tissue or may be otherwise under more precise environmental or developmental control. The most preferred vectors herein provided are expression vectors comprising a tightly-regulated inducible promoter operably linked to the nucleic acid compound. Also included is a vector which further comprises the plant resistance gene either operably linked to the tightly-regulated inducible promoter, or operably linked to a second, tightly-regulated inducible promoter. Generally, it will be beneficial to express the gene from an pathogen-inducible promoter. Such promoters include those from pathogeneis-related proteins (PR proteins), which are induced following infection by a pathogen, e.g. PR proteins, SAR proteins, beta-1,3 glucanase, chitinase, etc. See, for example, Redolfi et al., 89 *Neth J Plant Pathol* 245 (1983); Uknes et al., 4 *Plant Cell* 645 (1992); Van Loon, 4 *Plant Mol Virol* 111 (1985).

Of interest are promoters that are expressed locally at or near the site of pathogen infection. See, for example, Marineau et al., 9 *Plant Mol Biol* 335 (1987); Matton et al., 2 *Mol Plant-Microbe Interact* 325 (1989); Somsisch et al., 2 *Mol and Gen Genetics* 93 (1988). Yang, 93 *Proc Natl Acad Sci* 14972 (1996). See also, Chen et al., 10 *Plant J* 955 (1996); Zhang and Sing, 91 *Proc Natl Acad Sci USA* 2507 (1994); Warner et al., 3 *Plant J* 191 (1993); Siebertz et al., 1 *Plant Cell* 961 (1989); and the references cited therein. Of particular interest is the inducible promoter for the maize PRms gene, whose expression is induced by the pathogen *Fusarium moniliforme* (see, for example, Cordero et al, 41 *Physiol and Mol Plant Path* 189 (1992).

Additionally, because pathogens find entry into plants through wounds or insect damage, a wound-inducible promoter may be used in the contructions of the invention. Such wound inducible promoters include potato proteinase inhibitor (pin II) gene (Ryan, 28 *Annu Rev Phytopath* 425; Duan et al., 14 *Nature Biotech* 494; wun1 and wun2, U.S. Pat. No. 5,428,148; win1 and win2 (Stanford et al., 215 *Mol Gen Genet* 200; systemin (McGurl et al., 225 *Science* 1570; WIPI (Rohmeier et al., 22 *Plant Mol Biol* 783; Eckelkamp et al., 323 *FEBS Let* 73; MPI gene (Corderok et al., 6(2) *Plant J* 141 and references contained therein.

Construction of vectors comprising promoters in frame with nucleic acids is known in the art, and can be accomplished according to ie. Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993) A general method for the construction of any desired DNA sequence is provided in Brown et al., 68 *Methods in Enzymology* 109 (1979).

Environmental conditions that may effect transcription by inducible promoters include pathogen attack, anaerobic conditions, or the presence of light. Examples of inducible prometers are the Adh1 promoter which is inducible by hypoxia or cold stress, the Hsp70 promoter which is inducible by heat stress, and the PPDK promoter which is inducible by light. Examples of promoters under developmental control include promoters that initiate transcription only, or preferentially, in certain tissues, such as leaves, roots, fruit, seeds, or flowers. An exemplary promoter is the anther specific promter 5126 (U.S. Pat. Nos. 5,689,049 and 5,689,051). The operation of a promoter may also vary depending on its location in the genome. Thus, an inducible promoter may become fully or partially constitutive in certain locations.

Also included in the present invention are recombinant plant cells, recombinant seeds, recombinant plant embryos and recombinant plants comprising the vectors described herein.

Also provided are methods for constructing sequences with the ability to knockout the above sequences, comprising one of the following techniques: inserting a foreign piece of DNA into one of the disclosed sequences; deleting a piece of DNA from one of the disclosed sequences; rearranging the sequences (e.g. the repeats); or creating a mutation such that the avirulence activity is reduced or eliminated.

EXAMPLES

In vivo Translational Control Mediated by Specific Phosphorylation of the α Subunit of Plant Initiation Factor 2

MATERIALS AND METHODS

Plasmid Construction and Yeast Strains

Wild type wheat eIF2α is encoded within a 1.02 kb Nco1-BamH1 fragment. This cDNA was subcloned into the Nco1-Bam H1 site of pAlter-EX2 (Promega, Madison, Wis.). Single-stranded DNA was prepared and mutagenesis performed using the Altered Sites II in vitro system (Promega) with the following oligonucleotide (bold nucleotides indicate change): 5'TCTCCGAGCTCGCCCGC-CGCCGCATCC3' (SEQ ID NO 15). The resultant 51 serine to alanine mutant (51A) as well as the wild type 51 serine (51S) cDNA's were subcloned into the Nco1-BamH1 site of pET 30a+ (Novagen) and then into the low copy-number LEU2 plasmid pC76 in the NcoI, NotI sites to yield pC76-51A and pC76-51S (12). Sequencing confirmed the fidelity of the inserts.

Isogenic yeast strains H1643 (Mata ura3 leu2 trp1 sui2 (<GCN4-lacZ, TRP1>p[SUI2, URA3]) and H1925 (Mata ura3 leu2 trp1 sui2(gcn2(<GCN4-lacZ, TRP1>p[SUI2, URA3]) were transformed with pC76-51A, pC76-51S or with the empty vector according to standard methods: Dever, Cell 68: 585–596 (1992). Following transformation, p[SUI2, URA3] were evicted by plating on 5-FOA media. Strains transformed with pC76 alone failed to grow following 5-FOA plating. The successful eviction of p[SUI2, URA3] from transformants was further confirmed by the failure of resultant strains to grow on SD+Leu medium. Where indicated, selected strains were again transformed with the low copy number URA3 plasmid p703 or with p1054 a derivative of p703 containing the hyperactive GCN2c-517 allele (Dever et al.) Corresponding strains expressing yeast eIF2α 51S and 51A were a generous gift from T. Dever (NIH).

Growth Analysis

Analysis of strain growth was done by replica plating according to Dever et al. and by plating equal cell numbers onto solid media. Analyses were done using SD and YPD media (12) in the presence or absence of 3-aminotriazole (3-AT). 3-AT is a competitive inhibitor of histidine biosynthesis that induces the general amino acid control pathway (20). All plating experiments were repeated at least 3 times.

Analysis of in vivo Phosphorylation of eIF2α

Relative phosphorylation of plant eIF2α was analyzed by isoelectric focusing and by immunoblotting using antiserum generated against a phosphorylated eIF2α peptide (Research Genetics, Huntsville, Ala.). Essentially, cells were harvested following growth on the appropriate media in the absence or presence of 10 mM 3-AT for 6 hrs., lysed in buffer containing 40 mM Pipes (pH 6.5) and 100 mM NaCl, 2 mM PMSF, 1 mM DTT, 50 mM NaF and 40 mM b-glycerophosphate and crude protein extracted. Isoelectric focusing gels were prepared according to Dever, Methods 11: 403–417 (1997). Protein concentrations were determined using the BCA method (Pierce, Rockford, Ill.). A modified ECL method was used for immunoblotting (30). Experiments were repeated at least twice.

Assay of GCN4-lacZ Activity

Cells were grown to saturation in SD+Ura medium (SD for GCN2c-containing strains) followed by addition, where indicated, of 10 mM 3-AT and further incubation for 4 or 6 hr, respectively for cells grown in the absence or presence of 3-AT. Cells were harvested, washed and frozen at −20C. until use. Cells were lysed following thawing in buffer containing 0.1M Tris (pH 8.0), 20% glycerol, 1 mM 2 β-mercaptoethanol and proteins extracted. β-galactosidase assays were done according to Dever, Methods 11: 403–417 (1997) and protein concentrations determined by BCA methodology. Assays were done in duplicate and experiments were repeated at least 3 times.

Results

Plant eIF2 α Functionally Complements the Yeast SUI2 Gene Product Under GCN4 Repressing Conditions Wheat eIF2 is a heterotrimer composed of Mr 42,000 (a), 38,000 (b) and 50,000 (g) subunits whereas the corresponding yeast subunits are Mr 36,000 (a), 32,000 (b), 58,000(g). Plant eIF2α has significant sequence similarity to the yeast and human proteins in the regions surrounding the eIF2α kinase phosphorylation site and the putative kinase docking domain. However overall, plant eIF2α is only 51% identical to yeast eIF2α. In order to determine if plant eIF2α is capable of interacting with the guanine nucleotide exchange factor eIF2B within the context of a hybrid eIF2 holoenzyme and, if under appropriate conditions, it is capable of regulating translation in response to specific phosphorylation we subcloned cDNAs encoding the wild type and a 51A mutant of wheat eIF2α into a low copy number yeast expression vector containing a LEU marker. These were used to transform yeast strains deleted of the chromosomal SUT2 gene encoding eIF2α but containing SUI2 borne on a URA3 plasmid. Because eIF2α activity is required for cell survival, plasmid shuffling techniques were used to evict URA3 plasmids following transformation with the plasmids carrying wheat eIF2α constructs. Isolates successfully cured of the URA3 plasmid failed to grow on SD+Leu medium. Isogenic yeast strains carrying plasmid encoded genes for yeast eIF2α 51S and 51A were constructed in the same manner.

Steady state expressions of plant and yeast eIF2α 51S and 51A from the respective isogenic strains were measured by Western blotting and results showed comparable eIF2α protein levels. When equal number of cells were plated on SD+Ura medium that provide a nutrient rich environment, no substantial differences in growth at 3d were observed among strains expressing plant or yeast eIF2α 51S or the corresponding 51A proteins. In order to confirm these plating assays, growth rates of all strains were analyzed in liquid media. Following 48h, corresponding to saturation, no significant differences in growth rate were detected between the strains. Taken together these data indicate that plant eIF2α is capable of interacting with yeast b and g subunits of eIF2 to form a functional heterotrimer capable of ternary complex formation and initiation activity. Because eIF2–eIF2B interactions are mandatory for initiation and a resultant growth phenotype, these data also provide the first evidence that plant eIF2α interacts with eIF2B during guanine nucleotide exchange within the context of the eIF2 hybrid.

Plant eIF2α Complements Yeast eIF2α Under GCN4 Derepressing Conditions

Wild type wheat and yeast eIF2α proteins are specifically phosphorylated in vitro on serine 51 by GCN2. However, Krishna V M, Janaki N and Ramaiah K V A: Arch Biochem Biophys 346: 28–36 (1997), found that even though wheat germ eIF2α was phosphorylated in vitro, it did not mediate translational initiation in reticulocyte lysates thus, the in vivo significance of phosphorylation remains unclear. In order to address this issue in vivo, yeast strains expressing wheat eIF2α proteins were grown under conditions that induce activity of the endogenous eIF2α kinase GCN2. These conditions were created by the addition of 3-aminotriazole (3-AT), an inhibitor of histidine biosynthesis. Previous studies established that resistance to 3-AT requires an intact eIF2α phosphorylation pathway. Strains expressing wild type plant eIF2α were 3-AT resistant after 3d incubation. No significant difference was apparent between the growth of strains expressing wild type plant or yeast eIF2α. However, the ability to grow under nutrient starvation conditions was conferred by 51S and, by extension, phosphorylation because expression of the non-phosphorylatable mutant 51A of plant or yeast eIF2α inhibited strain growth under these conditions. During the course of this study it was noted that growth of strains expressing yeast 51A remained suppressed even after long term incubation while partial growth was observed in strains expressing plant 51A after 4d incubation.

Growth under nutrient starvation conditions is mediated by ternary complex formation that is conditioned not only by eIF2α phosphorylation but also by activity of the eIF2 holenzyme. The only eIF2α kinase in yeast is GCN2. Thus, it was important to evaluate the contribution of GCN2 activity. Isogenic (gcn2 strains were transformed with plant and yeast 51S and 51A constructs and following selection on 5-FOA, strains were plated on media in the presence and absence of 3-AT. The absence of GCN2 had no significant effect on strain growth under nutrient rich conditions. However, after 3 days incubation on media containing 30 mM 3-AT no growth was observed in strains expressing plant or yeast eIF2α 51S or 51A. After 4d, as previously observed, strains expressing plant constructs showed slight growth relative to strains expressing yeast 51S or 51A suggesting a partial GCN2 independent growth effect.

The GCN2 dependent growth response under nutrient starvation conditions was further evaluated in strains that constitutively express GCN2. Constitutive expression of GCN2 suppresses growth of strains expressing yeast eIF2α 51S under nutrient rich conditions due to decreased ternary complex formation resulting in a general decrease in protein synthesis. However, under starvation conditions yeast 51A-expressing strains are unable to grow whereas 51S strains grow albeit less than in a GCN2 background. Thus, the functional substitution of plant eIF2α would predict that strains expressing plant eIF2α 51S in a GCN2c background would show growth suppression under non-starvation but not under starvation conditions relative to 51A expressing strains. To test this prediction, strains containing plant eIF2α proteins were transformed with the GCN2c -517 allele, that is a dominant mutation resulting in high constitutive expression of GCN2. Growth of the 51S-expressing strain was suppressed on nutrient rich medium while the 51A strain was unaffected by the GCN2c -517 allele. However, under nutrient depravation conditions only the 51S strain was able to grow. Consistent with previous data, the 51A strain grew slightly on 3-AT medium following 4d incubation.

Plant eIF2α is Specifically Phosphorylated on Serine 51 by GCN2 In vivo

Plant eIF2α phosphorylation levels in the various strain backgrounds were directly determined under GCN4 repressing (non-starvation) and derepressing (starvation) conditions by isoelectric focusing and immunoblotting. Under GCN4 repressing conditions only a basic band was observed in GCN2 strains expressing either 51A or 51S indicating the presence of the unphosphorylated species (lanes 1, 3). No phosphorylated acidic band was detected under the isoelectric focusing conditions used or in immunoblotting experiments using antiserum that specifically recognizes the phosphorylated form of wheat eIF2α. This is in slight contrast to the results of Dever et al. who found that yeast eIF2α is normally present under nutrient rich conditions as phosphorylated and nonphosphorylated species but is hyperphosphorylated under GCN4 derepressing conditions. An additional more acidic band and a band corresponding to phosphorylated eIF2α was observed under starvation (GCN4 derepressing) conditions in GCN2 containing strains expressing plant 51S but not 51A. In the absence of GCN2, regardless of growth conditions, plant eIF2α was not phosphorylated (lanes 5–8). Further, in GCN2c-51S but not 51A strains eIF2α was phosphorylated, as expected, under GCN4 repressing and derepressing conditions, although phosphorylation levels increased under GCN4 derepressing conditions. These data confirm the specific in vivo GCN2-dependent phosphorylation of plant eIF2α and link phosphorylation with the ability of strains to grow under starvation conditions that require an intact general amino acid control pathway.

Phosphorylation of eIF2α Induces Expression of GCN4

GCN4 expression is an extremely sensitive indicator of ternary complex activity and thus provides a direct method to measure the impact of eIF2α phosphorylation on translation. Isogenic strains expressing wheat 51S or 51A contained a GCN4-lacZ fusion allowing measurement of β-galactosidase activity as a function of GCN4 expression level. Under starvation conditions GCN4 is expressed early prior to any phenotypic response. Table 1 shows that β-galactosidase activity dramatically increased in plant 51S expressing strains under nutrient starvation conditions relative to non-starvation conditions and that activity was GCN2 dependent. The GCN2 dependent nature of this response was supported by β-galactosidase measurements from (gcn2 and GCN2c strains. In the absence of GCN2, there were no significant differences between GCN4 expression level under derepressing or repressing conditions regardless of eIF2α species. Constitutive expression of GCN2 in 51S-containing strains caused a significant increase in β-galactosidase activity under non-starvation conditions relative to isogenic strains carrying GCN2. The 51A mutation that inhibits growth under amino acid starvation conditions also suppressed GCN4 expression relative to strains expressing plant 51S. These data are consistent with the functional substitution of wheat eIF2α in the yeast phosphorylation-mediated translational control pathway.

In vivo Regulation of Protein Synthesis by Phosphorylation of the a Subunit of Wheat Eukaryotic Initiation Factor 2

EXPERIMENTAL PROCEDURES

Materials

Chemicals were from Sigma (St. Louis, Mo.) unless otherwise specified. Polyclonal rabbit antibodies against plant eIF2 were a gift from Karen Browning (U. Austin, Tex.). Rabbit polyclonal antiserum recognizing specifically the phosphorylated form of both mammalian and plant eIF2α were purchased from Research Genetics (Huntsville, Ala.). Rabbit polyclonal antibodies directed against VV proteins have been used previously. Polyclonal rabbit antibody specific for PKR has been previously described. Secondary antibodies were purchased from Cappel (Durham, N.C.).

Plasmids

Wild type wheat eIF2α is encoded within a 1.02 kb NcoI-BamHI fragment. This cDNA was subcloned into the Nco1-BamH1 site of pAlter-EX2 (Promega, Madison, Wis.). Single-stranded DNA was prepared and mutagenesis performed using the Altered Sites II in vitro system (Promega) with the following oligonucleotide (bold nucleotides indicate change): 51A-5' TCT CCG AGC TCG CCC GCC GCC GCA TCC 3' (SEQ ID NO 15). The resultant 51 alanine mutant (51A) as well as the wild type 51 serine (51S) cDNA's were subcloned into the HindIII site of pBSII-SK (+) (Stratagene). Sequencing confirmed the fidelity of each eIF2α cDNA subcloned. Wheat eIF2α 51S and 51A cDNAs were excised from pBS-51S and pBS-51A, respectively, by digestion with Hind III. A 1.1 kb fragment was purified, repaired with Klenow and cloned into the hemagglutinin insertional VV vector pHLZ, previously digested with SmaI and dephosphorylated using alkaline phosphatase, to generate pHLZ-51A and pHLZ-51S, respectively. Sense orientation of the inserts was checked by restriction analysis.

Cells and Viruses

African green monkey kidney cells BSC-40 (ATCC CCL-26) were grown in Dulbecco's modified Eagle's medium (DMEM) supplemented with 10% heat-inactivated newborn calf serum (NCS). HeLa cells (ECACC 85060701) were grown in DMEM supplemented with 10% NCS. After mock inoculation or viral adsorption, cells were maintained with DMEM supplemented with 2% NCS. The recombinant VV PKR HA-virus expressing IPTG inducible PKR (called VV PKR for clarity in this study) was generated as described below by recombination of empty plasmid pHLZ (35) with WR 68K virus, expressing IPTG-inducible PKR. VV-α51S and VV-α51A were generated by homologous recombination of their respective pHLZ derived-plasmids with the western reserve (WR) strain of VV in BSC-40 cells, as previously described (36) and selected by blue plaque formation upon X-gal addition. VV PKR-α51S and VV PKR-α51A were generated by recombination of their respective pHLZ-based vectors with WR 68K virus, following standard procedures. Viruses were subjected to 5 rounds of plaque purification to generate homogenous recombinants.

Measurement of β-galactosidase Activity

Confluent BSC-40 cells seeded in 24 well plates were infected with 5 pfu per cell of the indicated viruses. After 1 h of viral adsorption 5 mM IPTG was added to induce PKR expression. Cells were collected at indicated times, resuspended in 100 ml of 0.25 M Tris, pH 7.8, and lysed by three freeze-thaw cycles. After lysis extracts were diluted to 1 ml with water, centrifugated and 10 ml of supernatant were used for β-galactosidase determination, performed in duplicate. 10 ml of cell lysate supernatants were mixed with 150 ml of chlorophenol red-b-D-galactopyranoside (CPRG) solution [1 mM Mg C12, 45 mM β-mercaptoethanol, 0.1 M sodium phosphate (pH 7.5), 5 mM CPRG] in a 96-well plate, incubated at 37° C. for 1 h and absorbance at 540 nm was determined. Experiments were repeated at least twice.

Measurement of Apoptosis

The Cell Death Detection Enzyme-linked immunosorbent assay (ELISA) kit (Roche) was used according to the manufacturer's instructions. This assay is based on the quantitative sandwich-enzyme-immunoassay-principle and uses mouse monoclonal antibodies directed against DNA and histones to estimate the amount of cytoplasmic histone-associated DNA.

For measurement of caspase-3 activity, 3×106 BSC-40 cells were collected, lysed in lysis buffer (150 mM KCl, 10% glycerol, 1 mM dithiothreitol, 5 mM magnesium acetate, 0.5% Nonidet P-40) and clarified by centrifugation. Equal amounts of supernatant and 2× reaction buffer (100 mM HEPES, pH 75, 20% glycerol, 5 mM dithiothreitol, 0.5 mM EDTA) were mixed and assayed for caspase-3 activity using as substrate 200 mM DEVD-pNA from Calbiochem. Free pNA produced by caspase activity was determined by measuring absorbance at 405 nm. All apoptosis analyses were repeated at least twice.

Metabolic Labeling of Proteins

BSC-40 cells cultured in 12 well plates were infected with the viruses indicated and rinsed 3 times with Met-Cys free DMEM 30 min. prior to labeling. Following incubation for an additional 30 min. at 37° C. with Met-Cys free DMEM, medium was removed and 50 mCi/ml of [35S] Met-Cys promix (Amersham) in Met-Cys free DMEM was added for an additional hour. After 3 washes with PBS, cells were harvested in lysis buffer. Protein concentrations were determined using the bicinchoninic acid assay (Pierce) with bovine serum albumin (BSA) as a standard. An aliquot of the cell lysate was diluted in 0.1 mg/ml BSA solution, proteins precipitated with 5% trichloroacetic acid (TCA) and collected on glass fiber filters using a vacuum manifold instrument (Millipore). Filters were dried and radioactivity counted in a scintillation counter using liquid scintillation cocktail. Experiments were repeated at least twice.

Immunoblotting

For immunoblot analysis, total cell extracts were boiled in Laemmli sample buffer and proteins were fractionated by 10% or 12% SDS-PAGE. After electrophoresis, proteins were transferred to nitrocellulose paper using a semidry blotting apparatus (Gelman Sciences). Filters were mixed with antiserum in PBS containing 5% non-fat dry milk (BLOTTO), incubated overnight at 4° C., washed 3 times with PBS and further incubated with secondary antibody coupled to horseradish peroxidase in BLOTTO. After washing with PBS, the immunocomplexes were detected using ECL Western blotting reagents (Amersham). Exposure of filters to Kodak X-OMAT films was performed for times varying from 3 seconds to 5 minutes, as needed. Experiments were repeated at least three times.

Plaque Assays

Confluent monolayers of BSC-40 cells grown in a 6-well plate were infected with 200 pfu/well of indicated viruses. After 1 h of viral adsorption, the inoculum was removed, cells washed and medium replaced by a mixture consisting of DMEM, 2% NCS and 0.9% agar, in the presence or absence of 5 mM IPTG as indicated. At 72 hpi, medium was removed and the monolayers were stained with 1% crystal violet in 2% ethanol. Experiments were repeated at least three times.

One-step Virus Growth Curves

Confluent monolayers of BSC-40 cells were infected with 5 pfu/cell of the indicated viruses. After 1 h the inoculum was removed, cells were washed twice with DMEM and DMEM+2% NCS and where indicated 5 mM IPTG was added to cells. At selected times cells were harvested, subjected to three freeze-thawing cycles and supernatants titrated by plaque assays using BSC-40 cells. Experiments were repeated at least three times.

Results

Figure 4:
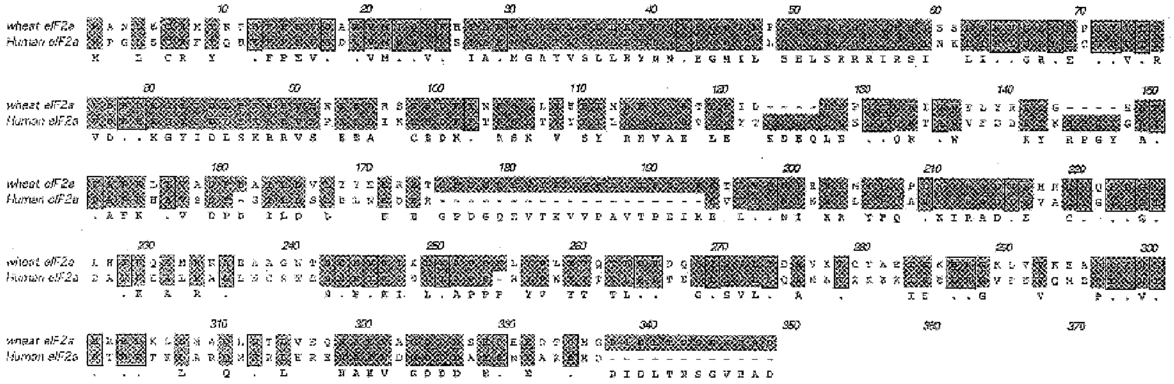
FIG. 4 Wild type (51S) wheat eIF2α (Seq ID No: 1) contains motifs associated with human eIF2α phosphorylation (Seq ID No: 3).

Wheat Wild Type eIF2α and Mutant 51A Proteins are Efficiently Expressed from Recombinant Vaccinia Viruses in Mammalian Cells Although only ca. 50% of the amino acid residues in the Mr 42,000 wild type (51S) wheat eIF2α are identical with residues in the Mr 36,000 human eIF2α it contains motifs associated with eIF2α phosphorylation (FIG. 4). Most importantly, the domain surrounding serine 51 and the KGYID putative kinase docking domain are entirely conserved. In order to determine if wheat eIF2α can function in the eIF2α phosphorylation pathway, we used a system based on the co-expression of the wheat protein together with PKR driven from VV recombinants. We have previously used PKR expressed from VV recombinants to check its function in the regulation of protein synthesis, antiviral activity induced following VV and vesicular stomatis virus infection and apoptosis induction. To analyze the function of plant eIF2α, wild type and nonphosphorylatable mutant (51A) cDNA's were subcloned into the VV vector pHLZ. Recombinant VV's were generated to allow the expression of51A or 51S from the HA locus under the control of a VV early-late synthetic promoter while PKR was inserted into the tk (thymidine kinase) locus of the virus genome under the control of a *Escherichia coli* lacI operator-repressor system-VV hybrid promoter allowing IPTG-inducible expression of PKR. Wheat eIF2α 51S and 51A proteins are constitutively expressed following infection of BSC-40 cells by recombinant vaccinia viruses VV PKR-α51S and VV PKR-α51A, respectively. Immunoblotting with antiserum that specifically recognized the Mr 42,000 plant eIF2α shows expression of the eIF2α proteins at 8 h and maximum accumulation at 24 h post-infection. The Mr 36,000 mammalian eIF2α did not cross-react with this antiserum. Although a background of PKR expression occurs in VV infected cells as a result of induction of endogenous PKR and leakiness of the system, PKR accumulation from VV PKR-α51S, VV PKR-α51A and VV PKR was significantly induced following IPTG treatment. IPTG-inducible PKR expression was observed at 8 hpi and levels continued to accumulate during infection. The decrease in 51S expression in cells treated with IPTG compared with uninduced cells is consistent with global decreases in protein synthesis following PKR induction and activation of the eIF2α phosphorylation pathway and has been observed for other proteins co-expressed together with PKR using this system. However, the expression pattern for 51A was only slightly altered by addition of IPTG suggesting that PKR mediated inhibition of protein synthesis is abrogated by 51A.

Plant eIF2α is Phosphorylated on Serine 51 by PKR in Mammalian Cells

Given the fact that the plant eIF2α wild-type and 51A mutant cDNA's are correctly expressed in mammalian cells alone or together with PKR, it was important to determine if wheat eIF2α is phosphorylated in vivo on the conserved serine 51 by PKR, a key requirement of the eIF2α translational regulation pathway. To this end, HeLa cells were infected with viruses expressing wheat 51A or 51S and the phosphorylation state of the peIF2α species was analyzed. Both proteins are expressed efficiently and, as noted previously, IPTG-induction of PKR provokes a decrease in steady state 51S levels (33% less than in the absence of IPTG), probably as a result of the block in protein synthesis caused by PKR expression. Although similar levels of 51A and 51S proteins were expressed, 51A was not recognized by the phosphorylation-state specific antibod. However, phosphorylated 51S was recognized by the antiserum. The detection of phosphorylated 51S in the absence of IPTG was likely due to leakage of the inducible system and by the presence of endogenous eIF2α kinases. However, the steady state level of wild type peIF2α(PO4) significantly increased when PKR expression was induced, even though 51S protein levels are lower than in the absence of PKR induction. Densitometric analyses of western blots showed that induction of PKR resulted in a 3.8-fold increase in phosphorylated peIF2α 51S relative to non-induced controls.

Expression of eIF2α 51A rescues PKR-mediated Antiviral Effects

Based upon the demonstration of in vivo PKR-mediated peIF2α phosphorylation and the fact that this is the hallmark of the PKR-based pathway for translational regulation, we next evaluated the ability of plant eIF2α to interfere with PKR antiviral activity in VV infected cells. Viral growth curves were determined in cells infected with the various VV recombinants in the presence or absence of IPTG. Induction of PKR resulted in a ca. 35-fold inhibition of VV replication at 24 h. These results are in agreement with those of Lee and Esteban. When a similar analysis was performed with VV PKR-α51S infected cells, the difference in viral yields between PKR induced and uninduced treatments was reduced (3-fold inhibition of VV replication at 24 h) compared to VV PKR infected cells. Significantly, no difference in viral yields was observed between PKR induced or uninduced treatments in cells infected with VV PKR-α51A, suggesting that expression of the nonphosphorylatable form of peIF2α suppressed the PKR-mediated eIF2α phosphorylation pathway. To confirm these observations, we compared plaque numbers from cells infected with the various viruses and cultured for 3 days in the continuous presence or absence of IPTG. As previously noted, a dramatic reduction in plaque number and size was observed in VV PKR infected cells growing in the presence of IPTG. A similar result was observed in cells infected with VV PKR-α51S. However, when plaque formation was analyzed in cells infected with VV PKR-α51A in the presence of IPTG, a rescue of approximately 50% of the plaques was observed. These data not only suggest that peIF2α 51A expression abrogates the PKR-mediated antiviral response but that wild type peIF2α 51S functions within the translation initiation mammalian pathway.

Expression of eIF2α 51A Abrogates the Translational Block Caused by PKR Expression The mechanism responsible for the PKR-mediated effects on viral growth in cells expressing wheat eIF2α 51S or wheat eIF2α 51A was evaluated by assaying protein synthesis patterns in the presence and absence of PKR induction. In mammalian cells, decreased VV pathogenesis as a result of PKR activation is correlated with a global decrease in protein synthesis. An initial and very sensitive determination of protein synthesis levels was made based upon expression of β-galactosidase driven from a VV 7.5 promoter incorporated in the VV recombinants. β-galactosidase production was severely inhibited (ca. 80%) in cells infected with VV PKR 20 h after IPTG treatment. Similarly, induction of PKR in cells infected with VV PKR-α51S inhibited β-galactosidase expression consistent with results from growth curve studies. However, β-galactosidase activity in cells expressing plant 51A was rescued from induction of PKR. This rescue could account for the absence of reduction in viral yields upon PKR expression and supports the concept that plant proteins are functionally interacting in the mammalian pathway.

In addition, specific VV protein production in cells infected with VV recombinants in the presence or absence of IPTG was determined to check if there was a correlation between levels of VV proteins expressed and the effect on viral yields. In VV PKR infected cells, addition of IPTG resulted in a severe decrease in steady state levels of VV proteins, specifically late viral proteins, since PKR expression was driven from a VV late promoter. Also a significant decrease in VV protein production at late times of infection was observed in cells infected with VV PKR-α51S when PKR was induced by IPTG treatment. However, this reduction was not observed in cells infected with VV PKR-α51A, supporting previous results.

Global Protein Synthesis Levels were Determined by Metabolically Labeling Cells Infected with VV Recombinants Followed by SDS-PAGE Analysis There was a significant decrease in protein synthesis in cells infected with VV PKR and VV PKR-α51S at late times (16 or 24 hpi) following PKR induction with IPTG. At earlier times (4 or 8 hpi) no differences were observed because active PKR only begins to accumulate at 10–12 hpi. This is consistent with the kinetics observed in experiments analyzing viral protein production and β-galactosidase activity. Similar results were observed in cells infected with VV PKR-α51S. However, in cells infected with the VV PKR-α51A recombinant, inhibition of protein synthesis was alleviated to a significant extent. In order to quantitate these results, labeled proteins were precipitated and counted in a scintillation counter. In cells infected with VV PKR or VV PKR-α51S, protein synthesis at 16 hpi decreased ca. 95% upon PKR induction relative to uninduced levels. However, expression of plant eIF2α-51A partially rescued the protein synthesis inhibition caused by PKR expression. In cells infected with VV-PKR α51A at 16 hpi there was a ca. 4-fold increase in protein synthesis compared with VV PKR infected cells. At 24 hpi in cells infected with VV PKR-α51A, there still was a 20% rescue of protein synthesis upon PKR induction compared with uninduced cells. These results are consistent with those of Gil et al. using mammalian eIF2α 51A and PKR coexpressed in infected cells from separate VV recombinants. Together these results strongly support the concept that a functional interference by the plant eIF2α 51A mutant helps to partially suppress the PKR-imposed translational block, causing also a reversion in antiviral effects induced by PKR expression.

PKR Induced Apoptosis is Decreased by Expression of Plant eIF2α 51A

Lee et al. showed that induction of PKR results in the development of apoptosis in cells infected with VV PKR. Recently, we and others also showed that inhibiting PKR-mediated phosphorylation of eIF2α by expression of mammalian eIF2α 51A resulted in a significant decrease in PKR-induced apoptosis. Thus, it was predicted that expression of plant eIF2α 51A would similarly inhibit PKR-induced apoptosis. In order to determine the effect of different doses of plant eIF2α while maintaining a constant PKR amount, we generated recombinant VV's expressing only the wheat eIF2α proteins (designated VV α51S and VV α51A). Thus, co-infection experiments to evaluate PKR-induced apoptosis could be performed with VV PKR and varying inoculum levels of VV α51S or VV α51A. Induction of PKR in cells infected with VV PKR resulted in apoptosis based upon analysis of caspase-3 activity and a photometric immunoassay for cytoplasmic histone-associated DNA fragments. A slight decrease in apoptosis induction was observed in cells expressing plant eIF2α 51S relative to controls consisting of cells infected with VV PKR. However, when plant eIF2α 51A was expressed, caspase-3 activity and DNA fragmentation were significantly reduced. This effect was dose dependent and at higher levels of 51A expression, the degree of apoptosis inhibition as measured by the caspase-3 assay was essentially identical to control cells infected solely with VV. Together these results suggest that, similarly to the mammalian homolog, expression of a non-phosphorylatable plant eIF2α mutant can block apoptosis induction triggered by PKR.

Interaction of Plant eIF2α 51S and 51A Proteins in the Mammalian Translational Initiation Apparatus In order to evaluate if the demonstrated effects of expression of plant eIF2α proteins in the VV system were due to a direct interaction with translational initiation, co-immunoprecipitation and co-localization experiments were preformed. When extracts from cells infected with VV PKR plant 51S or 51A were immunoprecipitated with anti-plant eIF2 serum and then subjected to western blotting with mammalian eIF2γ or eIF2β antiserum, that the mammalian proteins were specifically recognized. In contrast, in control experiments using lysates from cells infected with VV or VV PKR the mammalian subunits were not precipitated supporting a direct interaction between the plant and mammalian proteins. This interaction was further evaluated by purifying ribosomal fractions from VV PKR51S, VVPKR51A, VVPKR and VV infected cells and analyzing for the presence of the plant proteins. As these fractions contained translationally active complexes, identification of the plant proteins would suggest involvement in protein synthesis. Western blots show that plant eIF2α wild type and the 51A mutant are present in the ribosome fractions.

Protocol for Vacuum Infiltration Transformation of Arabidopsis

This protocol is adapted from protocols by Nicole Bechtold (Bechtold et al. 1993), Andrew Bent (Bent et al. 1994) and Takashi Araki. This protocol gives at least 95% of all infiltrated plants giving rise to transformants, and a transformant rate of 1–4% of seed.

1. Sow seeds of ecotype Columbia in lightweight plastic pots prepared in the following way: mound Arabidopsis soil mixture into pots (We use 3½ inch to 4 inch square pots), saturate soil with Arabidopsis fertilizer, add more soil so that it is rounded about 0.5 to 1 inch above the top, dust with fine vermiculite, cover soil with a square of window screen mesh (Circle Glass Co., Detroit, Mich.) and secure mesh with a rubber band.

2. Grow plants under conditions of 16 hours light/8 hours dark at 20° C. to 22° C., fertilizing from below with Arabidopsis fertilizer once a week, adding approximately 0.5" to each flat. Thin the plants to one per square inch or fewer per pot. After 4–6 weeks, depending on your conditions, plants will be ready to infiltrate when they are at this stage: the primary inflorescence is 5–15 cm tall and the secondary inflorescences are appearing at the rosette. No clipping of bolts is necessary before infiltration.

3. In the meantime, transform your construct into *Agrobacterium tumefaciens* strain C58C1 (pMP90) (Koncz and Schell 1986). When plants are ready to transform, inoculate a 500 ml culture of YEP medium containing 50 mg/L rifampicin, 25 mg/L gentamycin and the appropriate antibiotic for your construct with a 1 ml overnight starter culture. Be sure to water your plants well the day before infiltration so that the stomata will be open that day.

4. Grow culture overnight at 28° C. with shaking until culture OD600 is >2.0. Spin down the culture and resuspend it in 1 L of infiltration medium.

Infiltration medium (1 liter)

2.2 g MS salts

1×B5 vitamins 50 g sucrose 0.5 g MES pH to 5.7 with KOH 0.044 mM benzylaminopurine 200 ml Silwet L-77 (OSi Specialties request that purchases be made at Lehle Seeds, fax# (512) 388-3974 catalog #vis-01)

5. Place resuspended culture in a Rubbermaid container inside a vacuum desiccator. Invert pots containing plants to be infiltrated into the solution so that the entire plant is covered, including rosette, but not too much of the soil is submerged. One good way to do this is to place the corners of the pots on rubber stoppers sitting in the culture. Make sure no large bubbles are trapped under the plant.

6. Draw a vacuum of 400 mm Hg (about 17 inches). Once this level has been obtained, close the suction (i.e., so that the vacuum chamber is still under 17 inches of mercury but the vacuum is not still being directly pulled) and let the plants stay under vacuum for five minutes. Quickly release the vacuum. Briefly drain the pots, place them on their sides in a tray, cover tray with plastic wrap to maintain humidity, and place the flats back in a growth chamber. The next day, uncover the pots and set them upright. Keep plants infiltrated with different constructs in separate trays from this stage on.

7. Allow plants to grow under the same conditions as before (see step 2). Stake plants individually as the bolts grow. The leaves that were infiltrated will degenerate but continue growing plants until they finish flowering. Gradually reduce water and then stop watering to let them dry out. Harvest seed from each plant individually.

8. Prepare large selection plates: 4.3 g/L MS salts

1×B5 vitamins (optional)

1% sucrose 0.5 g/L MES pH to 5.7 with KOH 0.8% phytagar

Autoclave

Add antibiotics (50 mg/ml works well for kanamycin)

Pour into 150×15 mm plates

We also add vancomycin at 500 mg/L to control bacterial growth

9. Dry plates well in the sterile hood before plating. Twenty minutes to half an hour with the lids open is usually sufficient.

10. For each plant sterilize up to 100 ml of seeds (approximately 2500 seeds) and plate out individually. Sterilize seeds (7 minutes rocking in 50% bleach/0.02% Triton X-100, 3 rinses in sterile distilled water). Resuspend seeds in approximately 8 ml sterile 0.1% agarose and pour onto large selection plates as if plating phage. Tilt plate so seeds are evenly distributed, and let sit 10–15 minutes. After a while the liquid should soak into the medium; if evaporation is too slow, open the plate in the hood and let dry until the excess liquid is gone. Seal plats with Parafilm or paper surgical tape and place in a growth room.

11. After 5 to 7 days transformants will be visible as green plants. Transfer these onto "hard selection" plates (100×20 mm plates with same recipe as selection plates, but with 1.5% phytagar) this allows roots to elongate and eliminates and false positives. Place in growth room.

12. After 6–10 days, plants will have at least one set of true leaves. Transfer plants to soil, cover them with plastic, and move to a growth chamber with normal conditions. Keep covered for several days. Note: we usually move just one transformant to soil from any one plant that was infiltrated to ensure independent transformants.

REFERENCES

Bechtold N, Ellis J, Pelletier G (1993) C. R. Acad. Sci. Paris 316:1194–1199

Bent A, Kunkell B N, Dahlbeck D Brown K L, Schmidt R, Giraudat J, Leung J, Staskawicz B J (1994) Science 265:1856–1860

Koncz C, Schell J (1986) Mol. Gen. Genet. 204:383–396

YEP medium (1 liter)

10 g Bacto peptone 10 g yeast extract 5 g NaCl

1000×B5 vitamins (10 ml)

1000 mg myo-inositol 100 mg thiamine-HCl 10 mg nicotinic acid 10 mg pyridoxine-HCl Dissolve in ddH2O and store at −20° C.

Arabidopsis fertilizer (10 liters)

50 ml 1M KNO3

25 ml 1M KPO4 (pH 5.5)

20 ml 1M MgSO4

20 ml 1M Ca(NO3)2

5 ml 0.1M Fe EDTA 10 ml micronutrients (see below)

Dissolve in ddH2O and store at room temperature

Arabidopsis micronutrients (500 ml)

70 ml 0.5M boric acid 14 ml 0.5M MnCl2

2.5 ml 1M CuSO4

1 ml 0.5M ZnSO4

1 ml 0.1M NaMoO4

1 ml 5M NaCl 0.05 ml 0.1M CuCl2 Dissolve in ddH2O and store at room temperature

Production of Transgenic Tobacco

From: Horsch, R. B., J. Fry, N. Hoffmann, J. Neidermeyer, S. G. Rogers, & R. T. Fraley (1988) Leaf Disc Transformation Plant Molecular Biology Manual A5, 1–9

1. Remove leaves from young plants and place in 10% bleach plus 0.1% Tween 20 for 15 minutes.

2. Wash in sterile water three times.

3. Cut out leaf discs (using flamed 1 cm cork-borer) and place on MS104 media upside-down (place 3–5 discs per plate). We used 20–30 discs per treatment. Be careful to avoid excessive wounding in the process.

4. Incubate in growth chamber 24 hours.

5. On the same day the leaf discs are prepared, start an overnight culture of transformed Agrobacterium strains to be used (10 ml each in YEP media plus 100 mg/ml kanamycin).

6. The next day, pour the Agrobacterium culture into a sterile petri dish.

7. Transfer the leaf discs to the petri dish and quickly immerse in the Agrobacterium culture. Submerge only for 5 seconds. Do a control of non-infected leaf discs.

8. Transfer the discs onto sterile Whatmann 3MM paper and gently blot dry.

9. Return the discs to the MS/0 media plates and incubate for 24 hours.

10. After 24 hours, transfer the discs to MS+BA media supplemented with 500 mg/ml carbenicillin and 300 mg/ml kanamycin+500 mg/ml cefotaxime.

11. Wrap plates in parafilm and incubate several weeks (shoots form in approximately 1 week).

12. Plate onto MS/0+antibiotics and culture 8 weeks.

13. Plant to soil.

Recipes

YEP Media 10 g/L Bactopeptone 10 g/L Yeast Extract 5 g/L NaCl 15 g/L Bactoagar

MS104

4.3 g/L MS salts (GIBCO)

1 ml/L K3 vitamins (1000× stock)

30 g/L Sucrose 1 ml/L benzyladenine (BA)
(BA stock: 1 mg/ml in ethanol)

0.5 ml/L napthaleneacidic acid (NAA)
(NAA stock: 0.2 mg/ml in 1N NaOH)

Adjust pH to 5.7 add 8 g/L bactoagar and autoclave

MS/0

MS104 minus BA and NAA

Rooting Media 4.3 g/L MS salts (GIBCO)

1 ml/L K3 vitamins 30 g/L Sucrose

Adjust pH to 5.7 add 6 g/L bactoagar and autoclave

K3 Vitamins Stock (1000×)

100 mg/ml m-Inositol 1 mg/ml pyridoxine 10 mg/ml thiamine 1 mg/ml nicotinic acid Although the present invention has been fully described herein, it is to be noted that various changes and modifications are apparent to those skilled in the art. Such changes and modifications are to be understood as included within the scope of the present invention as defined by the appended claims.

What is claimed is:

1. A knock-out construct for knocking out the eIF2α gene in a higher plant, said construct comprising a nucleic acid encoding an eIF2α protein of SEQ ID NO: 1, wherein a serine at position 51 has been substituted with an amino acid selected from the group consisting of alanine and aspartic acid in said eIF2α encoding nucleic acid, said nucleic acid being capable of homologous recombination with the wild-type eIF2α gene in said higher plant.

2. A method for increasing protein translation in a plant, comprising the steps of:

(a) providing a nucleic acid construct which encodes an eIF2α protein of SEQ ID NO: 1 operably linked to an exogenous promoter sequence, said construct further comprising a selectable marker gene which confers resistance to a selection agent when expressed in a plant cell;

(b) contacting a plant cell with said construct under conditions whereby said construct enters said plant cell and expresses said nucleic acid encoding a eIF2α protein;

(c) selecting those plant cells that survive in the presence of said selection agent; and (d) regenerating a plant from said plant cell, wherein increase in protein translation is measured relative to protein translation in non-transformed plants of the same species at the same phase of growth as said plant expressing said exogenous eIF2α.

3. The method as claimed in claim 2, wherein said exogenous promoter is inducible.

4. The method as claimed in claim 3, the inducible promoter being selected from the group consisting of a pathogen-related promoter, an SAR promoter, a beta-1,3 glucanase promoter, a chitinase promoter, a maize Prms promoter, a potato proteinase inhibitor promoter, an Adh1 promoter, an hsp70 promoter, an PPDK promoter, and an anther specific promoter 5126.

5. The method as claimed in claim 2, wherein exogenous promoter activity is induced by a condition selected from the group consisting of pathogen attack, wounding, drought, hypoxia, light, high temperature and low temperature.

6. The method as claimed in claim 2, wherein said exogenous promoter is constitutive.

7. The method claimed in claim 2, wherein said plant is selected from the group consisting of rice, soybean, maize, beet, tobacco, wheat, barley, poppy, rape, sunflower, alfalfa, sorghum, rose, carnation, gerbera, carrot, tomato, lettuce, chicory, pepper, melon, cabbage, canola, tulip, orchid, lilly, ornamental plant, turfgrass, horticultural tree, forest tree, conifer, banana tree, grass for hay, fruit tree and bush.

8. A plant generated by the method of claim 2.

9. A method for decreasing protein translation in a plant, comprising the steps of:

(a) providing a nucleic acid construct which comprises a sequence encoding a mutant eIF2α protein of SEQ ID NO: 1 wherein a serine at position 51 has been substituted with a non-phosphorylatable amino acid, said sequence being operably linked to an exogenous promoter sequence, said construct further comprising a selectable marker gene which confers resistance to a selection agent when expressed in a plant cell;

(b) contacting a plant cell with said construct under conditions whereby said construct enters said plant cell and expresses said nucleic acid encoding said mutant eIF2α protein;

(c) selecting those plant cells that survive in the presence of said selection agent; and (d) regenerating a plant from said plant cell, wherein a decrease in protein translation is measured relative to protein translation in non-transformed plants of the same species at the same phase of growth as said plant expressing said mutant eIF2α.

10. The method as claimed in claim 9, wherein said serine at position 51 is substituted with an amino acid selected from the group consisting of alanine and aspartic acid.

11. The method as claimed in claim 9, wherein said exogenous promoter is inducible.

12. The method as claimed in claim 11, wherein the exogenous promoter activity is induced by a condition selected from the group consisting of pathogen attack, wounding, drought, hypoxia, light, high temperature and low temperature.

13. The method as claimed in claim 11, the inducible promoter being selected from the group consisting of a pathogen-related promoter, an SAR promoter, a beta-1,3 glucanase promoter, a chitinase promoter, a maize Prms promoter, a potato proteinase inhibitor promoter, an Adh1 promoter, an hsp70 promoter, an PPDK promoter, and an anther specific promoter 5126.

14. The method as claimed in claim 9, wherein said expression construct is constitutive.

15. The method claimed in claim 9, wherein said plant is selected from the group consisting of rice, soybean, maize, beet tobacco, wheat, barley, poppy, rape, sunflower, alfalfa, sorghum, rose, carnation gerbera, carrot, tomato, lettuce, chicory, pepper, melon, cabbage, canola, tulip, orchid and lilly, ornamental plant, turfgrass, horticultural tree, forest tree, conifer, banana tree, grass for hay, fruit tree and bush.

16. A plant generated by the method of claim 9.

* * * * *